United States Patent
Ni et al.

(10) Patent No.: US 6,566,498 B1
(45) Date of Patent: May 20, 2003

(54) HUMAN SERINE PROTEASE AND SERPIN POLYPEPTIDES

(75) Inventors: Jian Ni, Rockville, MD (US); Steven M. Ruben, Olney, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/244,111

(22) Filed: Feb. 4, 1999

Related U.S. Application Data

(60) Provisional application No. 60/073,961, filed on Feb. 6, 1998.

(51) Int. Cl.[7] .................. C07K 14/81; C12N 15/15; C12N 15/62; C12N 15/79
(52) U.S. Cl. ............. 530/350; 435/69.1; 435/252.3; 435/320.1; 514/2; 536/23.1
(58) Field of Search ................. 530/350; 514/2; 435/69.1, 252.3

(56) References Cited

U.S. PATENT DOCUMENTS 5,500,344 A    3/1996 Sayers et al. ............ 435/6

FOREIGN PATENT DOCUMENTS

| DE | 197 42 725 A1 | 4/1999 |
| EP | 0 887 414 A2 | 12/1998 |
| JP | 11225765 | 8/1999 |
| JP | 031487 | 1/2000 |
| WO | WO95/14772 | 6/1995 |
| WO | WO98/20165 | 5/1998 |
| WO | WO99/09138 | 2/1999 |
| WO | WO99/36550 A2 | 7/1999 |
| WO | WO99/46281 | 9/1999 |
| WO | WO99/47674 | 9/1999 |

OTHER PUBLICATIONS

Geneseq Accession No: R93087 (Aug. 27, 1996).
Genbank Accession No: AC004156 (Feb. 19, 1998).
Okubo, K. et al., Genomics, vol. 30 (2): 178–186 (1995).
Smyth et al., "Metase: Cloning and Distinct Chromosomal Location of a Serine Protease Preferentially Expressed in Human Natural Killer Cells," J. Immunol., 151(11):6195–6205 (1993).
Greer, Jonathan, "Comparative Modeling Methods: Applications to the Family of the Mammalian Serine Proteases," Proteins: Structure, Function, and Genetics, 7:317–334 (1990).
Whisstock et al., "An atlas of serpin conformations," TIBS (1998).
EMBL Accession No. L23134, "Homo Sapiens metase (MET–1) mRNA, complete cds."(Jan. 04, 1994).
Genseq Accession No. AAT19577, "Human gene signature HUMGS00642" (Jun. 27, 1996).

Primary Examiner—Ponnathapu Achutamurthy
Assistant Examiner—William W. Moore
(74) Attorney, Agent, or Firm—Human Genome Sciences, Inc.

(57) ABSTRACT

The present invention relates to novel human secreted proteins and isolated nucleic acids containing the coding regions of the genes encoding such proteins. Also provided are vectors, host cells, antibodies, and recombinant methods for producing human secreted proteins. The invention further relates to diagnostic and therapeutic methods useful for diagnosing and treating disorders related to these novel human secreted proteins.

42 Claims, 7 Drawing Sheets

```
HKAEF09

SEQ ID NO:9
    1 GGTCGACCCA CGCGTCCGTG CCCAGCCACC ACCGTCTCTC CAAAAACCCG AGGTCTCGCT
   61 AAAATCATCA TGGATTCACT TGGCGCCGTC AGCACTCGAC TTGGGTTTGA TCTTTTCAAA
  121 GAGCTGAAGA AAACAAATGA TGGCAACATC TTCTTTTCCC CTGTGGGCAT CTTGACTGCA
  181 ATTGGCATGG TCCTCCTGGG GACCCGAGGA GCCACCGCTT CCCAGTTGGA GGAGGTGTTT
  241 CACTCTGAAA AAGAGACGAA GAGCTCAAGA ATAAAGGCTG AAGAAAAAGA GGTGATTGAG
  301 AACACAGAAG CAGTACATCA ACAATTCCAA AAGTTTTTGA CTGAAATAAG CAAACTCACT
  361 AATGATTATG AACTGAACAT AACCAACAGG CTGTTTGGAG AAAAAACATA CCTCTTCCTT
  421 CAAAAATACT TAGATTATGT TGAAAAATAT TATCATGCAT CTCTGGAACC TGTTGATTTT
  481 GTAAATGCAG CCGATGAAAG TCGAAAGAAG ATTAATTCCT GGGTTGAAAG CAAAACAAAT
  541 GAAAAAATCA AGGACTTGTT CCCAGATGGC TCTATTAGTA GCTCTACCAA GCTGGTGCTG
  601 GTGAACATGG TTTATTTTAA AGGGCAATGG GACAGTTACG ATCTAGAGGC GGTCCTGGCT
  661 GCCATGGGGA TGGGCGATGC CTTCAGTGAG CACAAAGCCG ACTACTCGGG AATGTCGTCA
  721 GGCTCCGGGT TGTACGCCCA GAAGTTCCTG CACAGTTCCT TTGTGGCAGT AACTGAGGAA
  781 GGCACCGAGG CTGCAGCTGC CACTGGCATA GGCTTTACTG TCACATCCGC CCCAGGTCAT
  841 GAAAATGTTC ACTGCAATCA TCCCTTCCTG TTCTTCATCA GGAACCATGC ATCCCCAAAA
  901 CCAAGGAGCC CTGCCACCCC AAGGTGCCTG AGCCCTGCCA CCCCAAAGTG CCTGAGCCCT
  961 GCCAGCCCAA GGTTCCAGAG CCATGCCACC CCAAGGTGCC TGAGCCCTGC CCTTCAATAG
 1021 TCACTCCAGC ACCAGCCCAG CAGAAGACCA AGCAGAAGTA ATGTGGTCCA CAGCCATGCC
 1081 CTTGAGGAGC CGGCCACCAG ATGCTGAATC CCCTATCCCA TTCTGTGTAT GAGGTCCCAT
 1141 TTGCCCTTGC AATTGGCATT CTGCTCTCCCC CAAAAAAGAA TGTGCTATGA AGCTTTCTTT
 1201 CCTACACACT CTGAGTCTCT GAATGAAGCT GAAGGTCTTA GTACCCAGAG CTAGTTTTCA
 1261 GCTGCTCAGA ATTCATCTGA AGAGAGACTT AAGATGAAAG CAAATGATTC AGCTCCCTTA
 1321 TACCCCCATT AAATTCACTT TCAATTCCAA AAAAAAAAA AAAAAAAAA AAAAAAAAA
 1381 AAAAAAAAAA AAAAAAAAA AAAAA

Coding region - nucleotide 70 to 1017.

SEQ ID NO:10
MDSLGAVSTRLGFDLFKELKKTNDGNIFFSPVGILTAIGMVLLGTRGATASQLEEVFHSEKETKSSRIKAEEKEV
IENTEAVHQQFQKFLTEISKLTNDYELNITNRLFGEKTYLFLQKYLDYVEKYYHASLEPVDFVNAADESRKKINS
WVESKTNEKIKDLFPDGSISSSTKLVLVNMVYFKGQWDSYDLEAVLAAMGMGDAFSEHKADYSGMSSGSGLYAQK
FLHSSFVAVTEEGTEAAAATGIGFTVTSAPGHENVHCNHPFLFFIRNHASPKPRSPATPRCLSPATPKCLSPASP
RFQSHATPRCLSPALQ
```

Figure 1

HMWJH67

SEQ ID NO:1
CACGAGCGCCAGCCTGCGTCTGCCATGGGGCTCGGGTTGAGGGGCTGGGGACGTCCTCT
GCTGACTGTGGCCACCGCCCTGATGCTGCCCGTGAAGCCCCCGCAGGCTCCTGGGGGG
CCCAGATCATCGGGGGCCACGAGGTGACCCCCCACTCCAGGCCCTACATGGCATCCGTG
CGCTTCGGGGGCCAACATCACTGCGGAGGCTTCCTGCTGCGAGCCCGCTGGGTGGTCTC
GGCCGCCCACTGCTTCAGCCACAGAGACCTCCGCACTGGCCTGGTGGTGCTGGGCGCCC
ACGTCCTGAGTACTGCGGAGCCCACCCAGCAGGTGTTTGGCATCGATGCTCTCACCACG
CACCCCGACTACCACCCCATGACCCACGCCAACGACATCTGCCTGCTGCGGCTGAACGG
CTCTGCTGTCCTGGGCCCTGCAGTGGGGCTGCTGAGGCTGCCAGGGAGAAGGGCCAGGC
CCCCCACAGCGGGGACACGGTGCCGGGTGGCTGGCTGGGCTTCGTGTCTGACTTTGAG
GAGCTGCCGCCTGGACTGATGGAGGCCAAGGTCCGAGTGCTGGACCCGGACGTCTGCAA
CAGCTCCTGGAAGGGCCACCTGACACTTACCATGCTCTGCACCCGCAGTGGGGACAGCC
ACAGACGGGGCTTCTGCTCGGCCGACTCCGGAGGGCCCCTGGTGTGCAGGAACCGGGCT
CACGGCCTCGTTTCCTTCTCGGGCCTCTGGTGCGGCGACCCCAAGACCCCCGACGTGTA
CACGCAGGTGTCCGCCTTTGTGGCCTGGATCTGGGACGTGGTTCGGCGGAGCAGTCCCC
AGCCCGGCCCCTGCCTGGGACCACCAGGCCCCAGGAGAAGCCGCCTGAGCCACAACC
TTGCGGCATGCAAATGAGATGGCCGCTCCAGGCCTGGAATGTTCCGTGGCTGGGCCCCA
CGGGAAGCCTGATGTTCAGGGTTGGGGTGGGACGGGCAGCGGTGGGGCACACCCATTCC
ACATGCAAAGGGCAGAAGCAAACCCAGTAAAATGTTAACTGACAAAAAAAAAAAAAAAA

Coding:
ATGGGGCTCGGGTTGAGGGGCTGGGGACGTCCTCTGCTGACTGTGGCCACCGCCCTGAT
GCTGCCCGTGAAGCCCCCGCAGGCTCCTGGGGGGCCCAGATCATCGGGGGCCACGAGG
TGACCCCCCACTCCAGGCCCTACATGGCATCCGTGCGCTTCGGGGGCCAACATCACTGC
GGAGGCTTCCTGCTGCGAGCCCGCTGGGTGGTCTCGGCCGCCCACTGCTTCAGCCACAG
AGACCTCCGCACTGGCCTGGTGGTGCTGGGCGCCCACGTCCTGAGTACTGCGGAGCCCA
CCCAGCAGGTGTTTGGCATCGATGCTCTCACCACGCACCCCGACTACCACCCCATGACC
CACGCCAACGACATCTGCCTGCTGCGGCTGAACGGCTCTGCTGTCCTGGGCCCTGCAGT
GGGGCTGCTGAGGCTGCCAGGGAGAAGGGCCAGGCCCCCCACAGCGGGGACACGGTGCC
GGGTGGCTGGCTGGGCTTCGTGTCTGACTTTGAGGAGCTGCCGCCTGGACTGATGGAG
GCCAAGGTCCGAGTGCTGGACCCGGACGTCTGCAACAGCTCCTGGAAGGGCCACCTGAC
ACTTACCATGCTCTGCACCCGCAGTGGGGACAGCCACAGACGGGGCTTCTGCTCGGCCG
ACTCCGGAGGGCCCCTGGTGTGCAGGAACCGGGCTCACGGCCTCGTTTCCTTCTCGGGC
CTCTGGTGCGGCGACCCCAAGACCCCCGACGTGTACACGCAGGTGTCCGCCTTTGTGGC
CTGGATCTGGGACGTGGTTCGGCGGAGCAGTCCCCAGCCCGGCCCCTGCCTGGGACCA
CCAGGCCCCCAGGAGAAGCCGCCTGA SEQ ID NO:2
<u>MGLGLRGWGRPLLTVATALMLPVKPPAGSW</u>GAQIIGGHEVTPHSRPYMASVRFGGQHHC
GGFLLRARWVVSAAHCFSHRDLRTGLVVLGAHVLSTAEPTQQVFGIDALTTHPDYHPMT
HANDICLLRLNGSAVLGPAVGLLRLPGRRARPPTAGTRCRVAGWGFVSDFEELPPGLME
AKVRVLDPDVCNSSWKGHLTLTMLCTRSGDSHRRGFCSADSGGPLVCRNRAHGLVSFSG
LWCGDPKTPDVYTQVSAFVAWIWDVVRRSSPQPGPLPGTTRPPGEAA.

Figure 2

HKAET41

SEQ ID NO:3
GACCCACGCGTCCGGTACTGGGGCCTCCTCCACTGGGTCCGAATCAGTAGGTGACCCCG
CCCCTGGATTCTGGAAGACCTCACCATGGGACGCCCCGACCTCGTGCGGCCAAGACGT
GGATGTTCCTGCTCTTGCTGGGGGGAGCCTGGGCAGGGAAATACACAGTACGCCTGGGA
GACCACAGCCTACAGAATAAAGATGGCCCAGAGCAAGAAATACCTGTGGTTCAGTCCAT
CCCACACCCCTGCTACAACAGCAGCGATGTGGAGGACCACAACCATGATCTGATGCTTC
TTCAACTGCGTGACCAGGCATCCCTGGGGTCCAAAGTGAAGCCCATCAGCCTGGCAGAT
CATTGCACCCAGCTGGCCAGAAGTGCACCGTCTCAGGCTGGGGGCACTGTCACCAGTCC
CCGAGAGAATTTTCCTGACACTCTCAACTGTGCAGAAGTAAAATCTTTCCCCCAGAAGA
AGTGTGAGGATGCTTACCCGGGGCAGATCACAGATGGCATGGTCTGTGCAGGCAGCAGC
AAAGGGGCTGACACGTGCCAGGGCGATTCTGGAGGCCCCCTGGTGTGTGATGGTGCACT
CCAGGGCATCACATCCTGGGGCTCAGACCCCTGTGGGAGGTCCGACAAACCTGGCGTCT
ATACCAACATCTGCCGCTACCTGGACTGGATCAAGAAGATCATAGGCAGCAAGGGCTGA
TTTTAGGATAAGCACCGATCTCCCTTAATAAACTCACAACTCTCTGGTTCAAAAAAAAA
AAAAAAAAAAAAAAAAAAAAAAAA

Coding:
ATGGGACGCCCCCGACCTCGTGCGGCCAAGACGTGGATGTTCCTGCTCTTGCTGGGGGG
AGCCTGGGCAGGGAAATACACAGTACGCCTGGGAGACCACAGCCTACAGAATAAAGATG
GCCCAGAGCAAGAAATACCTGTGGTTCAGTCCATCCCACACCCCTGCTACAACAGCAGC
GATGTGGAGGACCACAACCATGATCTGATGCTTCTTCAACTGCGTGACCAGGCATCCCT
GGGGTCCAAAGTGAAGCCCATCAGCCTGGCAGATCATTGCACCCAGCTGGCCAGAAGTG
CACCGTCTCAGGCTGGGGGCACTGTCACCAGTCCCCGAGAGAATTTTCCTGACACTCTC
AACTGTGCAGAAGTAAAATCTTTCCCCCAGAAGAAGTGTGAGGATGCTTACCCGGGGCA
GATCACAGATGGCATGGTCTGTGCAGGCAGCAGCAAAGGGGCTGACACGTGCCAGGGCG
ATTCTGGAGGCCCCCTGGTGTGTGATGGTGCACTCCAGGGCATCACATCCTGGGGCTCA
GACCCCTGTGGGAGGTCCGACAAACCTGGCGTCTATACCAACATCTGCCGCTACCTGGA
CTGGATCAAGAAGATCATAGGCAGCAAGGGCTGA SEQ ID NO:4
MGRPRPRAAKTWMFLLLLGGAWAGKYTVRLGDHSLQNKDGPEQEIPVVQSIPHPCYNSS
DVEDHNHDLMLLQLRDQASLGSKVKPISLADHCTQLARSAPSQAGGTVTSPRENFPDTL
NCAEVKSFPQKKCEDAYPGQITDGMVCAGSSKGADTCQGDSGGPLVCDGALQGITSWGS
DPCGRSDKPGVYTNICRYLDWIKKIIGSKG

Figure 3

HKAFV61

SEQ ID NO:5
CGGGTCGACCCACGCGTCCGGGACGAGAGATAGCAGCGACGCGACAGGCCAAACAGTGA
CAGCCACGTAGAGGATCTGGCAGACAAAGAGACAAGACTTTGGAAGTGACCCACCATGG
GGCTCAGCATCTTTTTGCTCCTGTGTGTTCTTGGGCTCAGCCAGGCAGCCACACCGAAG
ATTTTCAATGGCACTGAGTGTGGGCGTAACTCACAGCCGTGGCAGGTGGGGCTGTTTGA
GGGCACCAGCCTGCGCTGCGGGGTGTCCTTATTGACCACAGGTGGGTCCTCACAGCGG
CTCACTGGCAGCGGCAGACCCATTCCCCGGATCTGCTCCAGTGCCTCAACCTCTCCATC
GTCTCCCATGCCACCTGCCATGGTGTGTATCCCGGGAGAATCACGAGCAACATGGTGTG
TGCAGGCGGCGTCCCGGGGCAAGATGCCTGCCAGGGTGATTCTGGGGGCCCCCTGGTGT
GTGGGGGAGTCCTTCAAGGTCTGGTGTCCTGGGGGTCTGTGGGGCCCTGTGGACAAGAT
GGCATCCCTGGAGTCTACACCTATATTTGCAAGTATGTGGACTGGATCCGGATGATCAT
GAGGAACAACTGACCTGTTTCCTCCACCTCCACCCCCACCCCTTAACTTGGGTACCCCT
CTGGCCCTCAGAGCACCAATATCTCCTCCATCACTTCCCCTAGCTCCACTCTTGTTGGC
CTGGGAACTTCTTGGAACTTTAACTCCTGCCAGCCCTTCTAAGACCCACGAGCGGGGTG
AGAGAAGTGTGCAATAGTCTGGAATAAATATAAATGAAGGAGGGAAAAAAAAAAAAAAA
AAAAAAAAAAAAA coding:
ATGGGGCTCAGCATCTTTTTGCTCCTGTGTGTTCTTGGGCTCAGCCAGGCAGCCACACC
GAAGATTTTCAATGGCACTGAGTGTGGGCGTAACTCACAGCCGTGGCAGGTGGGGCTGT
TTGAGGGCACCAGCCTGCGCTGCGGGGTGTCCTTATTGACCACAGGTGGGTCCTCACA
GCGGCTCACTGGCAGCGGCAGACCCATTCCCCGGATCTGCTCCAGTGCCTCAACCTCTC
CATCGTCTCCCATGCCACCTGCCATGGTGTGTATCCCGGGAGAATCACGAGCAACATGG
TGTGTGCAGGCGGCGTCCCGGGGCAAGATGCCTGCCAGGGTGATTCTGGGGGCCCCTG
GTGTGTGGGGGAGTCCTTCAAGGTCTGGTGTCCTGGGGGTCTGTGGGCCCTGTGGACA
AGATGGCATCCCTGGAGTCTACACCTATATTTGCAAGTATGTGGACTGGATCCGGATGA
TCATGAGGAACAACTGA SEQ ID NO:6
MGLSIFLLLCVLGLSQAATPKIFNGTECGRNSQPWQVGLFEGTSLRCGGVLIDHRWVLT
AAHWQRQTHSPDLLQCLNLSIVSHATCHGVYPGRITSNMVCAGGVPGQDACQGDSGGPL
VCGGVLQGLVSWGSVGPCGQDGIPGVYTYICKYVDWIRMIMRNN

Figure 4A

HETDK50

SEQ ID NO:7
TACGAGGTGGGTAGAGGTGATGCAGTGCTGAAGACCTGGGCCCCTGCTCAGTGCCTTTG
CTCTAGAATGGGTCCAGCTTGGCTTTGGCTACTGGGAACAGGGATCCTGGCCTCTGTCC
ACTGTCAGCCCCTTCTTGCCCATGGAGATAAAAGTCTGCAGGGGCCTCAACCCCCCAGG
CATCAGCTCTCAGAGCCAGCCCCCGCCTACCACAGAATCACACCCACCATTACCAATTT
TGCTTTGCGTTTGTATAAAGAGCTGGCAGCAGACGCCCCCGGAAACATCTTCTTCTCGC
CAGTGAGCATCTCCACCACCCTGGCCCTGCTCTCTCTTGGGGCCCAAGCTAACACCTCA
GCTCTGATCCTGGAGGGCCTGGGATTCAACCTCACAGAAACCCCTGAAGCCGACATCCA
CCAGGGCTTCCGGAGCCTCCTCCACACCCTTGCCCTGCCCAGCCCCAAACTCGAACTAA
AAGTAGGAAACTCCCTGTTCCTAGACAAGCGACTAAAGCCTCGGCAGCACTATTTGGAC
AGCATCAAGGAGCTTTATGGAGCTTTTGCTTTTTCTGCCAACTTCACAGATTCTGTTAC
AACTGGGAGGCAGATTAATGACTATTTGAGAAGGCAAACATACGGGCAAGTCGTGGACT
GCCTCCCGGAGTTCAGCCAGGACACGTTCATGGTTCTTGCCAATTACATCTTCTTCAAA
GCCAAGTGGAAGCACCCTTTCAGTCGCTACCAGACCCAGAAGCAGGAAAGTTTCTTTGT
GGATGAGAGGACTTCTCTCCAGGTCCCCATGATGCACCAAAAGGAAATGCACAGATTCC
TCTATGACCAGGATTTGGCTTGCACCGTCCTCCAGATAGAATACAGAGGAAATGCCTTG
GCGCTGCTGGTCCTCCCTGACCCGGGGAAAATGAAGCAGGTGGAGGCTGCTCTGCAGCC
ACAGACCCTGAGAAAATGGGGCCAATTGCTCCTGCCCAGTCTGTTGGATTTGCACTTGC
CAAGGTTTTCAATTTCTGGAACATATAACCTGGAAGACATACTTCCCCAAATTGGTCTC
ACCAACATACTCAACTTAGAAGCTGACTTCTCAGGAGTCACTGGGCAGCTCAACAAAAC
CATCTCCAAGGTGTCACACAAGGCGATGGTGGACATGAGTGAGAAGGGGACCGAGGCCG
GGGCTGCTTCAGGCCTCCTCTCCCAGCCCCATCTCTGAACACCATGTCAGACCCACAT
GCCCACTTCAACAGGCCTTTCCTCTTGCTCCTTTGGGAGGTCACCACCCAGAGCTTACT
CTTCCTGGGAAAAGTTGTCAACCCAGTTGCAGGGTAACCATGGTGGGAGGCCAGGAGTT
ATCTTATCTCATCCTGGACCAAACAGATAGGCCAGAACCAGCCTGCATCCTGGGGCTGC
TATGTGGTTCAGTTAATCAGTGTGCCAAGATTCTAATAAAGTTGACCTTGGGTTCTGTG
AAAAAAAAAAAAAAAAAAAAAAAAAAAAAAAAAAAAAAAAAAAAAAAAAAAA

Coding:
ATGGGTCCAGCTTGGCTTTGGCTACTGGGAACAGGGATCCTGGCCTCTGTCCACTGTCA
GCCCCTTCTTGCCCATGGAGATAAAAGTCTGCAGGGGCCTCAACCCCCCAGGCATCAGC
TCTCAGAGCCAGCCCCCGCCTACCACAGAATCACACCCACCATTACCAATTTTGCTTTG
CGTTTGTATAAAGAGCTGGCAGCAGACGCCCCCGGAAACATCTTCTTCTCGCCAGTGAG
CATCTCCACCACCCTGGCCCTGCTCTCTCTTGGGGCCCAAGCTAACACCTCAGCTCTGA
TCCTGGAGGGCCTGGGATTCAACCTCACAGAAACCCCTGAAGCCGACATCCACCAGGGC
TTCCGGAGCCTCCTCCACACCCTTGCCCTGCCCAGCCCCAAACTCGAACTAAAAGTAGG
AAACTCCCTGTTCCTAGACAAGCGACTAAAGCCTCGGCAGCACTATTTGGACAGCATCA
AGGAGCTTTATGGAGCTTTTGCTTTTTCTGCCAACTTCACAGATTCTGTTACAACTGGG
AGGCAGATTAATGACTATTTGAGAAGGCAAACATACGGGCAAGTCGTGGACTGCCTCCC
GGAGTTCAGCCAGGACACGTTCATGGTTCTTGCCAATTACATCTTCTTCAAAGCCAAGT
GGAAGCACCCTTTCAGTCGCTACCAGACCCAGAAGCAGGAAAGTTTCTTTGTGGATGAG
AGGACTTCTCTCCAGGTCCCCATGATGCACCAAAAGGAAATGCACAGATTCCTCTATGA
CCAGGATTTGGCTTGCACCGTCCTCCAGATAGAATACAGAGGAAATGCCTTGGCGCTGC
TGGTCCTCCCTGACCCGGGGAAAATGAAGCAGGTGGAGGCTGCTCTGCAGCCACAGACC
CTGAGAAAATGGGGCCAATTGCTCCTGCCCAGTCTGTTGGATTTGCACTTGCCAAGGTT
TTCAATTTCTGGAACATATAACCTGGAAGACATACTTCCCCAAATTGGTCTCACCAACA
TACTCAACTTAGAAGCTGACTTCTCAGGAGTCACTGGGCAGCTCAACAAAACCATCTCC
AAGGTGTCACACAAGGCGATGGTGGACATGAGTGAGAAGGGGACCGAGGCCGGGGCTGC
TTCAGGCCTCCTCTCCCAGCCCCATCTCTGAACACCATGTCAGACCCACATGCCCACT
TCAACAGGCCTTTCCTCTTGCTCCTTTGGGAGGTCACCACCCAGAGCTTACTCTTCCTG
GGAAAAGTTGTCAACCCAGTTGCAGGGTAA

Figure 4B

SEQ ID NO:8
MGPAWLWLLGTGILASVHCQPLLAHGDKSLQGPQPPRHQLSEPAPAYHRITPTITNFAL
RLYKELAADAPGNIFFSPVSISTTLALLSLGAQANTSALILEGLGFNLTETPEADIHQG
FRSLLHTLALPSPKLELKVGNSLFLDKRLKPRQHYLDSIKELYGAFAFSANFTDSVTTG
RQINDYLRRQTYGQVVDCLPEFSQDTFMVLANYIFFKAKWKHPFSRYQTQKQESFFVDE
RTSLQVPMMHQKEMHRFLYDQDLACTVLQIEYRGNALALLVLPDPGKMKQVEAALQPQT
LRKWGQLLLPSLLDLHLPRFSISGTYNLEDILPQIGLTNILNLEADFSGVTGQLNKTIS
KVSHKAMVDMSEKGTEAGAASGLLSQPPSLNTMSDPHAHFNRPFLLLLWEVTTQSLLFL
GKVVNPVAG

Figure 5

HKAEF09

SEQ ID NO:9

```
   1 GGTCGACCCA CGCGTCCGTG CCCAGCCACC ACCGTCTCTC CAAAAACCCG AGGTCTCGCT
  61 AAAATCATCA TGGATTCACT TGGCGCCGTC AGCACTCGAC TTGGGTTTGA TCTTTTCAAA
 121 GAGCTGAAGA AAACAAATGA TGGCAACATC TTCTTTTCCC CTGTGGGCAT CTTGACTGCA
 181 ATTGGCATGG TCCTCCTGGG GACCCGAGGA GCCACCGCTT CCCAGTTGGA GGAGGTGTTT
 241 CACTCTGAAA AAGAGACGAA GAGCTCAAGA ATAAAGGCTG AAGAAAAAGA GGTGATTGAG
 301 AACACAGAAG CAGTACATCA ACAATTCCAA AAGTTTTTGA CTGAAATAAG CAAACTCACT
 361 AATGATTATG AACTGAACAT AACCAACAGG CTGTTTGGAG AAAAAACATA CCTCTTCCTT
 421 CAAAAATACT TAGATTATGT TGAAAAATAT TATCATGCAT CTCTGGAACC TGTTGATTTT
 481 GTAAATGCAG CCGATGAAAG TCGAAAGAAG ATTAATTCCT GGGTTGAAAG CAAAACAAAT
 541 GAAAAAATCA AGGACTTGTT CCCAGATGGC TCTATTAGTA GCTCTACCAA GCTGGTGCTG
 601 GTGAACATGG TTTATTTTAA AGGGCAATGG GACAGTTACG ATCTAGAGGC GGTCCTGGCT
 661 GCCATGGGGA TGGGCGATGC CTTCAGTGAG CACAAAGCCG ACTACTCGGG AATGTCGTCA
 721 GGCTCCGGGT TGTACGCCCA GAAGTTCCTG CACAGTTCCT TTGTGGCAGT AACTGAGGAA
 781 GGCACCGAGG CTGCAGCTGC CACTGGCATA GGCTTTACTG TCACATCCGC CCCAGGTCAT
 841 GAAAATGTTC ACTGCAATCA TCCCTTCCTG TTCTTCATCA GGAACCATGC ATCCCCAAAA
 901 CCAAGGAGCC CTGCCACCCC AAGGTGCCTG AGCCCTGCCA CCCCAAAGTG CCTGAGCCCT
 961 GCCAGCCCAA GGTTCCAGAG CCATGCCACC CCAAGGTGCC TGAGCCCTGC CCTTCAATAG
1021 TCACTCCAGC ACCAGCCCAG CAGAAGACCA AGCAGAAGTA ATGTGGTCCA CAGCCATGCC
1081 CTTGAGGAGC CGGCCACCAG ATGCTGAATC CCCTATCCCA TTCTGTGTAT GAGGTCCCAT
1141 TTGCCCTTGC AATTGGCATT CTGTCTCCCC CAAAAAAGAA TGTGCTATGA AGCTTTCTTT
1201 CCTACACACT CTGAGTCTCT GAATGAAGCT GAAGGTCTTA GTACCCAGAG CTAGTTTTCA
1261 GCTGCTCAGA ATTCATCTGA AGAGAGACTT AAGATGAAAG CAAATGATTC AGCTCCCTTA
1321 TACCCCCATT AAATTCACTT TCAATTCCAA AAAAAAAAAA AAAAAAAAAA AAAAAAAAA
1381 AAAAAAAAAA AAAAAAAAAA AAAAA
```

Coding region - nucleotide 70 to 1017.

SEQ ID NO:10
MDSLGAVSTRLGFDLFKELKKTNDGNIFFSPVGILTAIGMVLLGTRGATASQLEEVFHSEKETKSSRIKAEEKEV
IENTEAVHQQFQKFLTEISKLTNDYELNITNRLFGEKTYLFLQKYLDYVEKYYHASLEPVDFVNAADESRKKINS
WVESKTNEKIKDLFPDGSISSSTKLVLVNMVYFKGQWDSYDLEAVLAAMGMGDAFSEHKADYSGMSSGSGLYAQK
FLHSSFVAVTEEGTEAAAATGIGFTVTSAPGHENVHCNHPFLFFIRNHASPKPRSPATPRCLSPATPKCLSPASP
RFQSHATPRCLSPALQ

Figure 6

HKABR62

SEQ ID NO:11
CCCACGCGTCCGGGCAACATGGGGTCCAGCAGCTTCTTGGTCCTCATGGTGTCTCTCGT
TCTTGTGACCCTGGTGGCTGTGGAAGGAGTTAAAGAGGGTATAGAGAAAGCAGGGGTTT
GCCCAGCTGACAACGTACGCTGCTTCAAGTCCGATCCTCCCCAGTGTCACACAGACCAG
GACTGTCTGGGGGAAAGGAAGTGTTGTTACCTGCACTGTGGCTTCAAGTGTGTGATTCC
TGTGAAGAACTGAAGAAGGAGGAAACAAGGATGAAGATGTGTCAAGGCCATACCCTGAG
CCAGGATGGGAAGGCCAAGTGTCCAGGCTCCTCCTCTACACCAGGTGTCCTCAGAAATG
ATGCTGGGTCCTTTCTACCTCTGGGGGTCATCTCACTTGGCACCTGCCCCTGAGGTCCT
GAGACTTGGAATATGGAAGAAGCAATACCCAACCCCACCAAAGAAAACCTGAGCTGAAG
TCCTTT

Coding:
ATGGGGTCCAGCAGCTTCTTGGTCCTCATGGTGTCTCTCGTTCTTGTGACCCTGGTGGC
TGTGGAAGGAGTTAAAGAGGGTATAGAGAAAGCAGGGGTTTGCCCAGCTGACAACGTAC
GCTGCTTCAAGTCCGATCCTCCCCAGTGTCACACAGACCAGGACTGTCTGGGGGAAAGG
AAGTGTTGTTACCTGCACTGTGGCTTCAAGTGTGTGATTCCTGTGAAGAACTGA SEQ ID NO:12
MGSSSFLVLMVSLVLVTLVAVEGVKEGIEKAGVCPADNVRCFKSDPPQCHTDQDCLGER
KCCYLHCGFKCVIPVKN.

HUMAN SERINE PROTEASE AND SERPIN POLYPEPTIDES

This application claims benefit under 35 U.S.C. §119(e) of now abandoned U.S. Provisional Patent Application Serial No. 60/073,961 filed Feb. 6, 1998, hereby incorporated herein by reference.

FIELD OF THE INVENTION

This invention relates to newly identified human polynucleotides and the polypeptides encoded by these polynucleotides, uses of such polynucleotides and polypeptides, and their production. More particularly the invention provides novel Serine Protease polypeptides, Serpin polypeptides and polynucleotides encoding such polypeptides.

BACKGROUND OF THE INVENTION

Localized proteolytic activity through the action of proteases plays a critical regulatory role in a variety of important biological processes. For instance, the enzyme plasmin plays such a role in hemostasis, angiogenesis, tumor metastisis, cellular migration and ovulation. Plasmin is generated from its precursor zymogen plasminogen by the action of plasminogen activators (PAs) such as tissue-type PA (t-PA) and urokinase-type (u-PA), both of which are serine proteases. The activity of the PA system is precisely regulated by several mechanisms, one of which involves the interaction of t-PA and u-PA with specific plasminogen activator inhibitors. Among these serine protease inhibitors (i.e., serpins), plasminogen activator inhibitor type 1 (PAI-1) is unique in its ability to efficiently inhibit u-PA as well as the single and two-chain forms of t-PA. High PAI-1 levels are associated with an increased risk of thromboembolic disease, while PAI-1 deficiency may represent an inherited autosomal recessive bleeding disorder. See, for instance, Reilly, T. M., et al., Recombinant plasminogen activator inhibitor type 1: a review of structural, functional, and biological aspects, *Blood Coag. And Fibrinolysis* 5:73–81 (1994).

Serpin Mechanism

The serpins are a gene family that encompasses a wide variety of protein products, including many of the proteinase inhibitors in plasma (Huber & Carrell, 1989; full citations of references cited in this section on Serpin Mechanism are listed at the end of this section). However, in spite of their name, not all serpins are proteinase inhibitors. They include steroid binding globulins, the prohormone angiotensinogen, the egg white protein ovalbumin, and barley protein Z, a major constituent of beer. The serpins are thought to share a common tertiary structure (Doolittle. 1983) and to have evolved from a common ancestor (Hunt & Dayhoff. 1980). Proteins with recognizable sequence homology have been identified in vertebrates, plants, insects and viruses but not, thus far, in prokaryotes (Huber & Carrell. 1989; Sasaki. 1991; Komiyama, Ray, Pickup, et al. 1994). Current models of serpin structure are based largely on seminal X-ray crystallographic studies of one member of the family, a-1-antitrypsin (a1AT), also called a-1-proteinase inhibitor (Huber & Carrell. 1989). The structure of a modified form of a1AT, cleaved in its reactive center, was solved by Loebermann and coworkers in 1984 (Loebermann, Tokuoka, Deisenhofer, & Huber. 1984). An interesting feature of this structure was that the two residues normally comprising the reactive center (Met-Ser), were found on opposite ends of the molecule, separated by almost 70 Å. Loebermann and coworkers proposed that a relaxation of a strained configuration takes place upon cleavage of the reactive center peptide bond, rather than a major rearrangement of the inhibitor structure. In this model, the native reactive center is part of an exposed loop, also called the strained loop (Loebermann, Tokuoka, Deisenhofer, & Huber. 1984; Carrell & Boswell. 1986; Sprang. 1992). Upon cleavage, this loop moves or "snaps back", becoming one of the central strands in a major b-sheet structure (b-sheet A). This transformation is accompanied by a large increase in thermal stability (Carrell & Owen. 1985; Gettins & Harten. 1988; Bruch, Weiss, & Engel. 1988; Lawrence, Olson, Palaniappan, & Ginsburg. 1994b).

Recent crystallographic structures of several native serpins, with intact reactive center loops, have confirmed Loebermann's hypothesis that the overall native serpin structure is very similar to cleaved a1AT, but that the reactive center loop is exposed above the plane of the molecule (Schreuder, de Boer, Dijkema, et al. 1994; Carrell, Stein, Fermi, & Wardell. 1994; Stein, Leslie, Finch, Turnell, McLaughlin, & Carrell. 1990; Wei, Rubin, Cooperman, & Christianson. 1994). Additional evidence for this model has come from studies where synthetic peptides, homologous to the reactive center loops of a1AT, antithrombin III (ATIII), or PAI-1 when added in trans, incorporate into their respective molecules, presumably as a central strand of b-sheet A (Björk, Ylinenjärvi, Olson, & Bock. 1992; Björk, Nordling, Larsson, & Olson. 1992; Schulze, Baumann, Knof, Jaeger, Huber, & Laurell. 1990; Carrell, Evans, & Stein. 1991; Kvassman, Lawrence, & Shore. 1995). This leads to an increase in thermal stability similar to that observed following cleavage of a serpin at its reactive center, and converts the serpin from an inhibitor to a substrate for its target proteinase. A third serpin structural form has also been identified, the so-called latent conformation. In this structure the reactive center loop is intact, but instead of being exposed, the entire amino-terminal side of the reactive center loop is inserted as the central strand into b-sheet A (Mottonen, Strand, Symersky, et al. 1992). This accounts for the increased stability of latent PAI-1 (Lawrence, Olson, Palaniappan, & Ginsburg. 1994a) as well as its lack of inhibitory activity (Hekman & Loskutoff. 1985). The ability to adopt this conformation is not unique to PAI-1, but has also now been shown for ATIII and a1AT (Carrell, Stein, Fermi, & Wardell. 1994; Lomas, Elliot, Chang, Wardell, & Carrell. 1995). Together, these data have led to the hypothesis that active serpins have mobile reactive center loops, and that this mobility is essential for inhibitor function (Lawrence, Strandberg, Ericson, & Ny. 1990; Carrell, Evans, & Stein. 1991; Carrell & Evans. 1992; Lawrence, Olson, Palaniappan, & Ginsburg. 1994b; Shore, Day, Francis-Chmura, et al. 1994; Lawrence, Ginsburg, Day, et al. 1995; Fa, Karolin, Aleshkov, Strandberg, Johansson, & Ny. 1995; Olson, Bock, Kvassman, et al. 1995). The large increase in thermal stability observed with loop insertion, is presumably due to reorganization of the five stranded b-sheet A from a mixed parallel-antiparallel arrangement to a six stranded, predominantly antiparallel b-sheet (Carrell & Owen. 1985; Gettins & Harten. 1988; Bruch, Weiss, & Engel. 1988; Lawrence, Olson, Palaniappan, & Ginsburg. 1994a). This dramatic stabilization has led to the suggestion that native inhibitory serpins may be metastable structures, kinetically trapped in a state of higher free energy than their most stable thermodynamic state (Lawrence, Ginsburg, Day, et al. 1995; Lee, Park, & Yu. 1996). Such an energetically unfavorable structure would almost certainly be subject to negative selection, and thus its retention in all inhibitory serpins implies that it has been conserved for functional reasons.

The serpins act as "suicide inhibitors" that react only once with a target proteinase forming an SDS-stable complex. They interact by presenting a "bait" amino acid residue, in their reactive center, to the enzyme. This bait residue is thought to mimic the normal substrate of the enzyme and to associate with the specificity crevice, or S1 site, of the enzyme (Carrell & Boswell. 1986; Huber & Carrell. 1989; Bode & Huber. 1994). The bait amino acid is called the P1 residue, with the amino acids toward the N-terminal side of the scissile reactive center bond labeled in order P1 P2 P3 etc. and the amino acids on the carboxyl side labeled P1' P2' etc. (Carrell & Boswell. 1986). The reactive center P1–P1' residues, appear to play a major role in determining target specificity. This point was dramatically illustrated by the identification of a unique human mutation, a1AT "Pittsburgh", in which a single amino acid substitution of Arg for Met at the P1 residue converted a1AT from an inhibitor of elastase to an efficient inhibitor of thrombin, resulting in a unique and ultimately fatal bleeding disorder (Owen, Brennan, Lewis, & Carrell. 1983). Numerous mutant serpins have been constructed, demonstrating a wide range of changes in target specificity, particularly with substitutions at P1 (York, Li, & Gardell. 1991; Strandberg, Lawrence, Johansson, & Ny. 1991; Shubeita, Cottey, Franke, & Gerard. 1990; Lawrence, Strandberg, Ericson, & Ny. 1990; Sherman, Lawrence, Yang, et al. 1992).

The exact structure of the complex between serpins and their target proteinases has been controversial. Originally it was thought that the complex was covalently linked via an ester bond between the active site serine residue of the proteinase and the new carboxyl-terminal end of the P1 residue, forming an acyl-enzyme complex (Moroi & Yamasaki, 1974; Owen, 1975; Cohen, Gruenke, Craig, & Geczy. 1977; Nilsson & Wiman. 1982). However, in the late 1980s and early 1990s it was suggested that this interpretation was incorrect, and that the serpin-proteinase complex is instead trapped in a tight non-covalent association similar to the so called standard mechanism inhibitors of the Kazal and Kunitz family (Longstaff & Gaffney, J. 1991; Shieh, Potempa, & Travis. 1989; Potempa, Korzus, & Travis. 1994). Alternatively, one study suggested a hybrid of these two models where the complex was frozen in a covalent but un-cleaved tetrahedral transition state configuration (Matheson, van Halbeek, & Travis. 1991). Recently however, new data by several groups have suggested that the debate has come full circle, with various studies using independent methods indicating that the inhibitor is indeed cleaved in its reactive-center and that the complex is most likely trapped as a covalent acyl-enzyme complex (Lawrence, Ginsburg, Day, et al. 1995; Olson, Bock, Kvassman, et al. 1995; Fa, Karolin, Aleshkov, Strandberg, Johansson, & Ny. 1995; Wilczynska, Fa, Ohlsson, & Ny. 1995; Lawrence, Olson, Palaniappan, & Ginsburg. 1994b; Shore, Day, Francis-Chmura, et al. 1994; Plotnick, Mayne, Schechter, & Rubin. 1996).

Recently, three groups have almost simultaneously proposed similar mechanisms for serpin inhibition (Lawrence, Ginsburg, Day, et al. 1995; Wilczynska, Fa, Ohlsson, & Ny. 1995; Wright & Scarsdale. 1995). This model suggests that upon encountering a target proteinase, a serpin binds to the enzyme forming a reversible complex that is similar to a Michaelis complex between an enzyme and substrate. Next, the proteinase cleaves the P1–P1' peptide bond resulting in formation of a covalent acyl-enzyme intermediate. This cleavage is coupled to a rapid insertion of the reactive center loop (RCL) into b-sheet A at least up to the P9 position. Since the RCL is covalently linked to the enzyme via the active-site Ser, this transition should also affect the proteinase, significantly changing its position relative to the inhibitor. If, during this transition, the RCL is prevented from attaining full insertion because of its association with the enzyme, and the complex becomes locked, with the RCL only partially inserted, then the resulting stress might be sufficient to distort the active site of the enzyme. This distortion would then prevent efficient deacylation of the acyl-enzyme intermediate, thus trapping the complex. However, if RCL insertion is prevented, or if deacylation occurs before RCL insertion then the cleaved serpin is turned over as a substrate and the active enzyme released. This means that what determines whether a serpin is an inhibitor or a substrate is the ratio of $k_{diss}$ to $k_{stab}$. If deacylation ($k_{diss}$) is faster than RCL insertion ($k_{stab}$) then the substrate reaction predominates. However, if RCL insertion and distortion of the active site can occur before deacylation then the complex is frozen as a covalent acyl-enzyme. A similar model was first proposed in 1990 (Lawrence, Strandberg, Ericson, & Ny. 1990) and is consistent with studies demonstrating that RCL insertion is not required for proteinase binding but is necessary for stable inhibition (Lawrence, Olson, Palaniappan, & Ginsburg. 1994b) as well as the observation that only an active enzyme can induce RCL insertion (Olson, Bock, Kvassman, et al. 1995). Very recently, direct evidence for this model was provided by Plotnick et al., who by NMR observed an apparent distortion of an enzyme's catalytic site in a serpin-enzyme complex (Plotnick, Mayne, Schechter, & Rubin. 1996). In conclusion, these data suggest that serpins act as molecular springs where the native structure is kinetically trapped in a high energy state. Upon association with an enzyme some of the energy liberated by RCL insertion is used to distort the active site of the enzyme, preventing deacylation and trapping the complex.

During the development of the nervous system, neurons form axons which extend along a prespecified path into the target area, where they engage in the formation and refinement of synaptic connections. These stages depend critically on the capability of the axonal growth cones to interact with a variety of structures which they encounter along their way and at their destination. These structures include cell surfaces of neuronal and non-neuronal origin and the extracellular matrix. Along their trajectory and at their target sites, growth cones not only receive and respond to signals from their local environment, but also actively secrete macromolecules. In particular, secreted proteases have been implicated in supporting the growth cone advancement through the tissue. More than a decade ago, it was demonstrated that plasminogen activators are axonally secreted by neurons in culture. Recently, their occurrence in the developing rat nervous system during the period of axon outgrowth has been revealed. Moreover, several pieces of evidence were presented which indicated that serine proteases, such as plasminogen activators or thrombin, are involved in restructuring of the synaptic connectivity during development and regeneration. Such processes include elimination during development and synaptic plasticity associated with learning and memory in the adult. See, for instance, Osterwalder, T., et al., "Neuroserpin, an axonally secreted serine protease inhibitor," *EMBO J.* 15:2944–2953 (1996).

During normal development of the nervous system, about 50% of postmitotic lumbosacral motoneurons undergo naturally occurring (programmed) cell death during a period when these cells are forming synaptic connections with their target muscles. Naturally occurring motoneuron death has been described in many vertebrate species, including chicken, mouse, rat, and human embryos or fetuses. For example, programmed motoneuron death occurs between embryonic day (E)6 and E10 in the chicken. This system has been used as a biological model for testing different neurotrophic agents on motoneuron survival in vivo. See, for instance, Houenou, L. J., et al., "A serine protease inhibitor, protease nexin I, rescues motoneurons from naturally occurring and axotomy-induced cell death," *Proc. Natl. Acad. Sci. USA* 92:895–899 (1995).

Although programmed cell death is completed before birth in mammals, the maintenance of motoneurons continues to be dependent on support from the target for some time after birth. Thus, if transection of motor axons is performed in neonatal mammals and reinnervation is prevented, a large number of motoneurons degenerate and die. Axotomy-induced death of motoneurons has also been extensively used as a model for testing the survival effects of various agents, including neurotrophic and growth factors on motoneurons.

Protease nexin I (PNI), also known as glia-derived nexin, is a 43–47-kDa protein that was first found secreted by cultured fibroblasts but is also produced by glial (glioma and primary) and skeletal muscle cells. PNI has been shown to promote neurite outgrowth from different neuronal cell types. These include neuroblastoma cells, as well as primary hippocampal and sympathetic neurons. The neurite-promoting activity of PNI in vitro is mediated by inhibition of thrombin, a potent serine protease. PNI (mRNA and protein) is transiently up-regulated in rat sciatic nerve after axotomy, and PNI-producing cells are localized distal to the lesion site. This up-regulation of PNI occurs 2–3 days after a similar up-regulation of prothrombin and thrombin in the distal stump. Free PNI protein is significantly decreased, while endogenous PNI-thrombin complexes are increased, in various anatomical brain regions, including hippocampus of patients with Alzheimer disease. When considered together with the recent demonstration that PNI can promote the in vitro survival of mixed mouse spinal chord neurons and that PNI is released from glia cells by neuropeptides such as vasoactive intestinal polypeptide, these observations suggest that PNI may play a physiological role in neuronal survival, differentiation, and/or axonal regeneration in vivo.

Recently, it has been reported that PNI rescues spinal motoneuron death in the neonatal mouse. Houenou, L. J. et al., 1995, supra. The survival effect of PNI on motoneurons during the period of programmed cell death was not associated with increased intramuscular nerve branching. PNI also significantly increased the nuclear size of motoneurons during the period of programmed cell death and prevented axotomy-induced atrophy of surviving motoneurons. These results indicate a possible role of PNI as a neurotrophic agent. They also support the idea that serine proteases or, more precisely, the balance of proteases and serpins may be involved in regulating the fate of neuronal cells during development.

More recently, a cDNA encoding an axonally secreted glycoprotein of central nervous system (CNS) and peripheral nervous system (PNS) neurons of the chicken has been cloned and sequenced. Osterwalder, T., et al., 1996) supra. Analysis of the primary structural features characterized this protein as a novel member of the serpin superfamily which was therefore called "neuroserpin." No demonstration of inhibition of any protease was included in this report, however. In situ hybridization revealed a predominately neuronal expression during the late stages of neurogenesis and in the adult brain in regions which exhibit synaptic plasticity. Thus, it has been suggested that neuroserpin may function as an axonally secreted regulator of the local extracellular proteolysis involved in the reorganization of the synaptic connectivity during development and synapse plasticity in the adult. A role for serine proteases and serpins in neuronal remodeling is further supported by the finding that elevated tPA mRNA and protein levels are found in cerebellar Purkinje neurons of rats undergoing motor learning (Seeds N W; Williams B L; Bickford P. C., "Tissue plasminogen activator induction in Purkinje neurons after cerebellar motor learning." *Science* 270:1992–4 (1995)).

The amplification of a human cDNA fragment of about 450 bp corresponding to the region of the chicken cDNA encoding the putative reactive site loop of the so-called neuroserpin, using a polymerase chain reaction with two pairs of nested primers flanking that region, has also been reported. Osterwalder, T., et al., 1996, supra, page 2946. The authors also reported that the deduced amino acid sequences of the human and corresponding mouse cDNA exhibited a sequence identity of 88% and 87% respectively, with chicken neuroserpin. No nucleotide or amino acid sequence was reported for this human cDNA. However, the present inventors are not aware of any other public disclosure of full length cDNA sequence data for a human counterpart of the chicken neuroserpin cDNA or polypeptide.

Thus, there is a need for human polypeptides that function as serpins in the regulation of various serine proteases, particularly in the nervous system, since disturbances of such regulation may be involved in disorders relating to hemostasis, angiogenesis, tumor metastisis, cellular migration and ovulation, as well as neurogenesis; and, therefore, there is a need for identification and characterization of such human polypeptides which can play a role in preventing, ameliorating or correcting such disorders.

SUMMARY OF THE INVENTION

The present invention relates to novel polynucleotides and the encoded polypeptides. Moreover, the present invention relates to vectors, host cells, antibodies, and recombinant methods for producing the polypeptides and polynucleotides. Also provided are diagnostic methods for detecting disorders related to the polypeptides, and therapeutic methods for treating such disorders. The invention further relates to screening methods for identifying binding partners of the polypeptides.

BRIEF DESCRIPTION OF THE DRAWINGS

FIG. 1 shows the nucleotide sequence (SEQ ID NO:1) of the human cDNA in clone HMWJH67 and the deduced amino acid sequence (SEQ ID NO:2) encoded thereby.

FIG. 2 shows the nucleotide sequence (SEQ ID NO:3) of the human cDNA in clone HKAET41 and the deduced amino acid sequence (SEQ ID NO:4) encoded thereby.

FIG. 3 shows the nucleotide sequence (SEQ ID NO:5) of the human cDNA in clone HKAFV61 and the deduced amino acid sequence (SEQ ID NO:6) encoded thereby.

FIG. 4 shows the nucleotide sequence (SEQ ID NO:7) of the human cDNA in clone HETDK50 and the deduced amino acid sequence (SEQ ID NO:8) encoded thereby.

FIG. 5 shows the nucleotide sequence (SEQ ID NO:9) of the human cDNA in clone HKAEF09 and the deduced amino acid sequence (SEQ ID NO:10) encoded thereby.

FIG. 6 shows the nucleotide sequence (SEQ ID NO:11) of the human cDNA in clone HKABR62 and the deduced amino acid sequence (SEQ ID NO:12) encoded thereby.

DETAILED DESCRIPTION

Definitions

The following definitions are provided to facilitate understanding of certain terms used throughout this specification.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide.

In the present invention, a "secreted" protein refers to those proteins capable of being directed to the ER, secretory vesicles, or the extracellular space as a result of a signal sequence, as well as those proteins released into the extracellular space without necessarily containing a signal sequence. If the secreted protein is released into the extracellular space, the secreted protein can undergo extracellular processing to produce a "mature" protein. Release into the extracellular space can occur by many mechanisms, including exocytosis and proteolytic cleavage.

As used herein, a "polynucleotide" refers to a molecule having a nucleic acid sequence contained in SEQ ID NO:X or the cDNA contained within the clone deposited with the ATCC. For example, the polynucleotide can contain the nucleotide sequence of the full length cDNA sequence, including the 5' and 3' untranslated sequences, the coding region, with or without the signal sequence, the secreted protein coding region, as well as fragments, epitopes, domains, and variants of the nucleic acid sequence. Moreover, as used herein, a "polypeptide" refers to a molecule having the translated amino acid sequence generated from the polynucleotide as broadly defined.

In the present invention, the full length sequence identified as SEQ ID NO:X was often generated by overlapping sequences contained in multiple clones (contig analysis). A representative clone containing all or most of the sequence for SEQ ID NO:X was deposited with the American Type Culture Collection ("ATCC"). As shown in Table 1, each clone is identified by a cDNA Clone ID (Identifier) and the ATCC Deposit Number. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure.

A "polynucleotide" of the present invention also includes those polynucleotides capable of hybridizing, under stringent hybridization conditions, to sequences contained in SEQ ID NO:X, the complement thereof, or the cDNA within the clone deposited with the ATCC. "Stringent hybridization conditions" refers to an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 $\mu$g/ml denatured, sheared salmon sperm DNA, followed by washing the filters in 0.1×SSC at about 65° C.

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37° C. in a solution comprising 6×SSPE (20×SSPE=3M NaCl; 0.2M $NaH_2PO_4$; 0.02M EDTA, pH 7.4), 0.5% SDS, 30% formamide, 100 ug/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone).

The polynucleotide of the present invention can be composed of any polyribonucleotide or polydeoxribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formulation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1–12 (1983); Seifter et al., Meth Enzymol 182:626–646 (1990); Rattan et al., Ann NY Acad Sci 663:48–62 (1992).)

"SEQ ID NO:X" refers to a polynucleotide sequence while "SEQ ID NO:Y" refers to a polypeptide sequence, both sequences identified by an integer specified in Table 1.

"A polypeptide having biological activity" refers to polypeptides exhibiting activity similar, but not necessarily identical to, an activity of a polypeptide of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about tenfold less activity, and most preferably, not more than about three-fold less activity relative to the polypeptide of the present invention.)

Polynucleotides and Polypeptides of the Invention
Features of Proteins Encoded by SEQ ID NOS: 1, 3 and 5

Each of the polypeptides shown as SEQ ID NOS:2, 4 and 6 herein are members of the Serine Protease polypeptide family. This determination has been made based on the strong degree of sequence similarity each of the polypeptides share with other members of the Serine Protease family. The predicted translation product of the human cDNA in clone HMWJH67 (SEQ ID NO:2) shows a high degree of sequence similarity to putative Preproadipsin [Sus scrofa domestica] (Genbank accession no. gi|915533); the predicted translation product of the human cDNA in clone HKAET41 (SEQ ID NO:4) shows a high degree of sequence similarity to Protease M [Homo sapiens] (gi|1518788), Neuropsin [Homo sapiens] (gnl|PID|d1011968), and Serine Protease [Homo sapiens] (gi|2318115); and the predicted translation product of the human cDNA in clone HKAFV61 (SEQ ID NO:6) shows a high degree of sequence similarity to Neuropsin [Mus musculus] (gnl|PID|d1007022). Thus, the polypeptides showns as SEQ ID NOS:7–9 and those encoded by cDNA clones HMWJH67, HKAFV61, and HKAET41, are expected to share serine protease activities common to other members of the serine protease family. Such activity may be measured by assays known to those of skill in the art, and assays referenced and described elsewhere herein.

Human cDNA clone HMWJH67 was isolated from a cDNA library derived from the human bone marrow cell line RS4;11. Human cDNA clones HKAET41 and HKAFV61 were isolated from a cDNA library derived from human keratinocyte tissue.

Serine protease inhibitors, such as an antagonist of the serine proteases of the invention (e.g. an antibody), may be used to inhibit the action of serine proteases, for example, in the treatment of disorders characterized by degradation of the extracellular matrix, such as, e.g., cancer, arthritis, cardiovascular disorders, cachexia, immune system disorders, digestive disorders and multiple sclerosis.

Serine proteases themselves are useful in the development of antagonsists, e.g., antibodies. Assays for identifying antagonsists of protease activity are described elsewhere herein and are well known in the art.

Features of Proteins Encoded by SEQ ID NOS:7, 9 and 11

Each of the polypeptides shown as SEQ ID NOS:8, 10 and 12 herein are members of the Serpin polypeptide family. This determination has been made based on the strong degree of sequence similarity each of the polypeptides described herein share with other members of the Serpin polypeptide family. The predicted translation product of HETDK50 (SEQ ID NO:8) shows a high degree of sequence similarity to Pre-alpha-1-antitrypsin precursor [Homo sapiens] (gi|177822); the predicted translation product of HKAEF09 (SEQ ID NO:10) shows a high degree of sequence similarity to Squamous Cell Carcinoma Antigen [Homo sapiens] (gi|1172087); and the predicted translation product of HKABR62 (SEQ ID NO:12) shows a high degree of sequence similarity to Secretory Leukocyte Protease Inhibitor [Mus musculus] (gi|1763263).

Human cDNA clone HETDK50 was isolated from a cDNA library derived from human endometrial tumor tissue. Human cDNA clones HKAEF09 and HKABR62 were isolated from a cDNA library derived from human keratinocyte tissue.

Based on the identification of these polypeptides as Serpins, they are expected to be useful to treat wasting associated with excessive protease production during inflammation or diseases associated with nervous tissue degeneration. For example, neuronal loss is associated with such diseases as Kallmann's and Down's syndromes, and Alzheimer's and Huntington's diseases may also be treated by administration of these novel serpin polypeptides. The serpins may also be used to decrease the amount of free circulating somatostatin to prevent somatostatin's inhibitory effect on the release of growth hormone. Further, serpins may be used to remove excess levels of prolactin in the treatment of galactorrhea and/or hypogandism.

As noted above, the Serpin polynucleotides, polypeptides of this invention are useful for diagnosis of various nervous system-related disorders in mammals, including impaired processes of learning and memory, including impaired spatial, olfactory and taste-aversion learning, learning and memory impairments associated with Alzherimer's disease, and the like. Given the activities modulated by such Serpin polypeptides, it is readily apparent that a substantially altered (increased or decreased) level of expression of a Serpin polypeptide of the invention in an individual compared to the standard or "normal" level produces pathological conditions such as those described above in relation to diagnosis of nervous system-related disorders. It will also be appreciated by one of ordinary skill that, since the Serpin proteins of the invention are translated with a leader peptide suitable for secretion of the mature protein from the cells which express such proteins, when a Serpin protein (particularly the mature form) is added from an exogenous source to cells, tissues or the body of an individual, the protein will exert its modulating activities on any of its target cells of that individual. Therefore, it will be appreciated that conditions caused by a decrease in the standard or normal level of a Serpin activity in an individual, or an increase in a protease susceptible to inhibition by the Serpin, particularly disorders of the nervous system, can be treated by administration of such Serpin protein.

As noted above, one member in the serpin family is protease nexin I (PNI) or glia-derived nexin (GDN) which has been shown to inhibit thrombin specifically and to promote, in vitro, neurite extension in neuroblastoma cell lines as well as primary hippocampal, and sympathetic neurons. The PNI gene is induced transcriptionally and protein levels are increased following rat sciatic nerve axotomy. Other neurotrophic factors like nerve growth factor, brain-derived neurotrophic factor, and insulin-like growth factor I respond likewise to peripheral nerve damage. Treatment of chick developing motoneurons, i.e. E6–E9 lumbrosacral motoneurons which normally undergo apoptosis, with PNI results in increased survival of motoneurons. Motoneuron death experimentally induced by sciatic nerve lesioning in mouse is also decreased by PNI addition. Alzheimer-diseased brain regions contain higher PNI/thrombin complexes compared with free PNI than do normal brains suggesting that PNI may have a role in CNS pathology.

Thus, due to the similarities in amino acid sequence and tissue localization between the Serpin polypeptides of this invention and PNI, the Serpins can be used for treating peripheral neuropathies such as ALS or multiple sclerosis. Motoneuron or sensory neuron damage resulting from spinal cord injury also my be prevented by treatment with the Serpin proteins of this invention. In addition, central nervous system diseases like Alzheimer's disease may be treated with a Serpin or, preferably, a small molecule analog capable of crossing the blood-brain barrier, which analog can be identified according to the methods of the present invention.

the nervous system. Similarly, a product called Trasylol (aprotinin), a protease inhibitor, is being marketed by Bayer for bleeding disorders. The beneficial action of this serine protease inhibitor in limiting blood loss after cardiopulmonary bypass has been widely reported. The Serpin polypeptides of this invention are likewise useful during surgical procedures.

PNI has been shown to inhibit breakdown of extracellular matrix in a fibroblast tumor cell line . Such breakdown is thought to enable tumor cells to metastasize by weakening of extracellular matrix which normally prevents penetration of unrelated cells through a tissue. The presently claimed Serpin polypeptides also may be used to inhibit extracellular matrix destruction associated with tumors secreting a Serpin-susceptible protease, for instance, neural tissue tumors secreting t-PA.

Table 1, above, summarizes the information corresponding to each "Gene No." described above.

The cDNA Clone ID was deposited on the date and given the corresponding deposit number listed in "ATCC Deposit No:Z and Date." "Vector" refers to the type of vector into which the human cDNA has been inserted.

"Total NT Seq." refers to the total number of nucleotides in the contig identified by "Gene No." The deposited clone may contain all or most of these sequences, reflected by the nucleotide position indicated as "5' NT of Clone Seq." and the "3' NT of Clone Seq." of SEQ ID NO:X. The nucleotide position of SEQ ID NO:X of the putative start codon (methionine) is identified as "5' NT of Start Codon." Similarly, the nucleotide position of SEQ ID NO:X of the predicted signal sequence is identified as "5' NT of First AA of Signal Pep."

| Protein ID (Group-Nr) | cDNA Clone ID | ATCC Deposit Nr and Date | Vector | NT SEQ ID NO: X | Total NT Seq. | 5' NT of Clone Seq. | 3' NT of Clone Seq. | NOTE | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|---|
| PF391-1 | HMWJH67 | 209644 02/25/98 | Uni-ZAP XR | 1 | 1062 | 1 | 1062 | | 25 | 25 | 2 | 1 | 31 | 32 | 283 |
| PF391-2 | HKAET41 | 209644 02/25/98 | pCMVSport 2.0 | 3 | 792 | 1 | 792 | | 85 | 85 | 4 | 1 | 23 | 24 | 207 |
| PF391-3 | HKAFV61 | 209644 02/25/98 | pCMVSport 2.0 | 5 | 840 | 1 | 840 | | 115 | 115 | 6 | 1 | 17 | 18 | 162 |
| PF391-4 | HETDK50 | 209644 02/25/98 | Uni-ZAP XR | 7 | 1527 | 1 | 1527 | | 67 | 67 | 8 | 1 | 19 | 20 | 422 |
| PF391-5 | HKAEF09 | 209644 02/25/98 | pCMVSport 2.0 | 9 | 1405 | 1 | 1405 | | 70 | 70 | 10 | 1 | 49 | 50 | 316 |
| PF391-6 | HKABR62 | 209644 02/25/98 | pCMVSport 2.0 | 11 | 478 | 1 | 478 | | 19 | 19 | 12 | 1 | 19 | 20 | 76 |

Aside from the nervous system-related disorders described above, under diagnostic uses of the invention based on detecting Serpin expression, the protease inhibitory activity of a Serpin protein of the present invention also indicates that this protein may be used for therapeutic treatment of other conditions where excessive proteolytic activity of a Serpin susceptible protease may be involved, particularly t-PA. Thus, BAIT may be used to modulate the process of clot breakdown, for instance, in combination with Activase (recombinant t-PA) which Genentech is marketing for clot dissolution after stoke. A major problem with the present Activase therapy is that frequently excessive hemorrhaging occurs. The Serpins of this invention provide a specific inhibitor of t-PA which would fine tune the treatment process and not interact with other serine proteases in The translated amino acid sequence, beginning with the methionine, is identified as "AA SEQ ID NO:Y," although other reading frames can also be easily translated using known molecular biology techniques. The polypeptides produced by these alternative open reading frames are specifically contemplated by the present invention.

The first and last amino acid position of SEQ ID NO:Y of the predicted signal peptide is identified as "First AA of Sig Pep" and "Last AA of Sig Pep." The predicted first amino acid position of SEQ ID NO:Y of the secreted portion is identified as "Predicted First AA of Secreted Portion." Finally, the amino acid position of SEQ ID NO:Y of the last amino acid in the open reading frame is identified as "Last AA of ORF."

SEQ ID NO:X and the translated SEQ ID NO:Y are sufficiently accurate and otherwise suitable for a variety of uses well known in the art and described further below. For instance, SEQ ID NO:X is useful for designing nucleic acid hybridization probes that will detect nucleic acid sequences contained in SEQ ID NO:X or the cDNA contained in the deposited clone. These probes will also hybridize to nucleic acid molecules in biological samples, thereby enabling a variety of forensic and diagnostic methods of the invention. Similarly, polypeptides identified from SEQ ID NO:Y may be used to generate antibodies which bind specifically to the proteins encoded by the cDNA clones identified in Table 1.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:X and the predicted translated amino acid sequence identified as SEQ ID NO:Y, but also a sample of plasmid DNA containing a human cDNA of the invention deposited with the ATCC, as set forth in Table 1. The nucleotide sequence of each deposited clone can readily be determined by sequencing the deposited clone in accordance with known methods. The predicted amino acid sequence can then be verified from such deposits. Moreover, the amino acid sequence of the protein encoded by a particular clone can also be directly determined by peptide sequencing or by expressing the protein in a suitable host cell containing the deposited human cDNA, collecting the protein, and determining its sequence.

The present invention also relates to the genes corresponding to SEQ ID NO:X, SEQ ID NO:Y, or the deposited clone. The corresponding gene can be isolated in accordance with known methods using the sequence information disclosed herein. Such methods include preparing probes or primers from the disclosed sequence and identifying or amplifying the corresponding gene from appropriate sources of genomic material.

Also provided in the present invention are species homologs. Species homologs may be isolated and identified by making suitable probes or primers from the sequences provided herein and screening a suitable nucleic acid source for the desired homologue.

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the secreted protein, including the mature form, or may be a part of a larger protein, such as a fusion protein (see below). It is often advantageous to include an additional amino acid sequence which contains secretory or leader sequences, prosequences, sequences which aid in purification , such as multiple histidine residues, or an additional sequence for stability during recombinant production.

The polypeptides of the present invention are preferably provided in an isolated form, and preferably are substantially purified. A recombinantly produced version of a polypeptide, including the secreted polypeptide, can be substantially purified by the one-step method described in Smith and Johnson, Gene 67:31–40 (1988). Polypeptides of the invention also can be purified from natural or recombinant sources using antibodies of the invention raised against the protein in methods which are well known in the art.

Signal Sequences

Methods for predicting whether a protein has a signal sequence, as well as the cleavage point for that sequence, are available. For instance, the method of McGeoch, Virus Res. 3:271–286 (1985), uses the information from a short N-terminal charged region and a subsequent uncharged region of the complete (uncleaved) protein. The method of von Heinje, Nucleic Acids Res. 14:4683–4690 (1986) uses the information from the residues surrounding the cleavage site, typically residues –13 to +2, where +1 indicates the amino terminus of the secreted protein. The accuracy of predicting the cleavage points of known mammalian secretory proteins for each of these methods is in the range of 75–80%. (von Heinje, supra.) However, the two methods do not always produce the same predicted cleavage point(s) for a given protein.

In the present case, the deduced amino acid sequence of the secreted polypeptide was analyzed by a computer program called SignalP (Henrik Nielsen et al., Protein Engineering 10:1–6 (1997)), which predicts the cellular location of a protein based on the amino acid sequence. As part of this computational prediction of localization, the methods of McGeoch and von Heinjc are incorporated. The analysis of the amino acid sequences of the secreted proteins described herein by this program provided the results shown in Table 1.

As one of ordinary skill would appreciate, however, cleavage sites sometimes vary from organism to organism and cannot be predicted with absolute certainty. Accordingly, the present invention provides secreted polypeptides having a sequence shown in SEQ ID NO:Y which have an N-terminus beginning within 5 residues (i.e., + or –5 residues) of the predicted cleavage point. Similarly, it is also recognized that in some cases, cleavage of the signal sequence from a secreted protein is not entirely uniform, resulting in more than one secreted species. These polypeptides, and the polynucleotides encoding such polypeptides, are contemplated by the present invention.

Moreover, the signal sequence identified by the above analysis may not necessarily predict the naturally occurring signal sequence. For example, the naturally occurring signal sequence may be further upstream from the predicted signal sequence. However, it is likely that the predicted signal sequence will be capable of directing the secreted protein to the ER. These polypeptides, and the polynucleotides encoding such polypeptides, are contemplated by the present invention.

Polynucleotide and Polypeptide Variants

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown in Table 1, the ORF (open reading frame), or any fragement specified as described herein.

As a practical matter, whether any particular nucleic acid molecule or polypeptide is at least 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identiy are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the lenght of the subject nucleotide sequence, whichever is shorter.

If the subject sequence is shorter than the query sequence because of 5' or 3' deletions, not because of internal deletions, a manual correction must be made to the results. This is becuase the FASTDB program does not account for 5' and 3' truncations of the subject sequence when calculating percent identity. For subject sequences truncated at the 5' or 3' ends, relative to the the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/ alignement of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequnce are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequences shown in Table 1 or to the amino acid sequence encoded by deposited DNA clone can be determined conventionally using known computer programs. A preferred method for determing the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is becuase the FASTDB program does not account for N- and C-terminal truncations of the subject sequence when calculating global percent identity. For subject sequences truncated at the N- and C-termini, relative to the the query sequence, the percent identity is corrected by calculating the number of residues of the query sequence that are N- and C-terminal of the subject sequence, which are not matched/ aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequnce are manually corrected for. No other manual corrections are to made for the purposes of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5–10, 1–5, or 1–2 amino acids are substituted, deleted, or added in any combination are also preferred. Polynucleotide variants can be produced for a variety of reasons, e.g., to optimize codon expression for a particular host (change codons in the human mRNA to those preferred by a bacterial host such as *E. coli*).

Naturally occurring variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the protein without substantial loss of biological function. The authors of Ron et al., J. Biol. Chem. 268: 2984–2988 (1993), reported variant KGF proteins having heparin binding activity even after deleting 3, 8, or 27 amino-terminal amino acid residues. Similarly, Interferon gamma exhibited up to ten times higher activity after deleting 8–10 amino acid residues from the carboxy terminus of this protein. (Dobeli et al., J. Biotechnology 7:199–216 (1988).)

Moreover, ample evidence demonstrates that variants often retain a biological activity similar to that of the naturally occurring protein. For example, Gayle and coworkers (J. Biol. Chem 268:22105–22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See, Abstract.) In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the secreted form will likely be retained when less than the majority of the residues of the secreted form are removed from the N-terminus or C-terminus. Whether a particular polypeptide lacking N- or C-terminal residues of a protein retains such immunogenic activities can readily be determined by routine methods described herein and otherwise known in the art.

Thus, the invention further includes polypeptide variants which show substantial biological activity. Such variants, include deletions, insertions, inversions, repeats, and substitutions selected according to general rules known in the art so as have little effect on activity. For example, guidance concerning how to make phenotypically silent amino acid substitutions is provided in Bowie, J. U. et al., Science 247:1306–1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

Besides conservative amino acid substitution, variants of the present invention include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36: 838–845 (1987); Cleland et al., Crit. Rev. Therapeutic Drug Carrier Systems 10:307–377 (1993).)

Polynucleotide and Polypeptide Fragments

In the present invention, a "polynucleotide fragment" refers to a short polynucleotide having a nucleic acid sequence contained in the deposited clone or shown in SEQ ID NO:X. The short nucleotide fragments are preferably at least about 15 nt, and more preferably at least about 20 nt, still more preferably at least about 30 nt, and even more preferably, at least about 40 nt in length. A fragment "at least 20 nt in length," for example, is intended to include 20 or more contiguous bases from the cDNA sequence contained in the deposited clone or the nucleotide sequence shown in SEQ ID NO:X. These nucleotide fragments are useful as diagnostic probes and primers as discussed herein. Of course, larger fragments (e.g., 50, 150, 500, 600, 2000 nucleotides) are preferred.

Moreover, representative examples of polynucleotide fragments of the invention, include, for example, fragments having a sequence from about nucleotide number 1–50, 51–100, 101–150, 151–200, 201–250, 251–300, 301–350, 351–400, 401–450, 451–500, 501–550, 551–600, 651–700, 701–750, 751–800, 800–850, 851–900, 901–950, 951–1000, 1001–1050, 1051–1100, 1101–1150, 1151–1200, 1201–1250, 1251–1300, 1301–1350, 1351–1400, 1401–1450, 1451–1500, 1501–1550, 1551–1600, 1601–1650, 1651–1700, 1701–1750, 1751–1800, 1801–1850, 1851–1900, 1901–1950, 1951–2000, or 2001 to the end of SEQ ID NO:X or the cDNA contained in the deposited clone. In this context "about" includes the particularly recited ranges, larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein.

In the present invention, a "polypeptide fragment" refers to a short amino acid sequence contained in SEQ ID NO:Y or encoded by the cDNA contained in the deposited clone. Protein fragments may be "free-standing," or comprised within a larger polypeptide of which the fragment forms a part or region, most preferably as a single continuous region. Representative examples of polypeptide fragments of the invention, include, for example, fragments from about amino acid number 1–20, 21–40, 41–60, 61–80, 81–100, 102–120, 121–140, 141–160, or 161 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges, larger or smaller by several (5, 4, 3, 2, or 1) amino acids, at either extreme or at both extremes.

Preferred polypeptide fragments include the complete protein as well as the mature form. Further preferred polypeptide fragments include the complete protein or the mature form having a continuous series of deleted residues from the amino or the carboxy terminus, or both. For example, any number of amino acids, ranging from 1–60, can be deleted from the amino terminus of either the secreted polypeptide or the mature form. Similarly, any number of amino acids, ranging from 1–30, can be deleted from the carboxy terminus of the protein or mature form. Furthermore, any combination of the above amino and carboxy terminus deletions are preferred. Similarly, polynucleotide fragments encoding these polypeptide fragments are also preferred.

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta arnphipathic regions, flexible regions, surface-forming regions, substrate binding region, and high antigenic index regions. Polypeptide fragments of SEQ ID NO:Y falling within conserved domains are specifically contemplated by the present invention. Moreover, polynucleotide fragments encoding these domains are also contemplated.

Other preferred fragments are biologically active fragments. Biologically active fragments are those exhibiting activity similar, but not necessarily identical, to an activity of the polypeptide of the present invention. The biological activity of the fragments may include an improved desired activity, or a decreased undesirable activity.

Epitopes & Antibodies

In the present invention, "epitopes" refer to polypeptide fragments having antigenic or immunogenic activity in an animal, especially in a human. A preferred embodiment of the present invention relates to a polypeptide fragment comprising an epitope, as well as the polynucleotide encoding this fragment. A region of a protein molecule to which an antibody can bind is defined as an "antigenic epitope." In contrast, an "immunogenic epitope" is defined as a part of a protein that elicits an antibody response. (See, for instance, Geysen et al., Proc. Natl. Acad. Sci. USA 81:3998–4002 (1983).)

Fragments which function as epitopes may be produced by any conventional means. (See, e.g., Houghten, R. A., Proc. Natl. Acad. Sci. USA 82:5131–5135 (1985) further described in U.S. Pat. No. 4,631,211.)

In the present invention, antigenic epitopes preferably contain a sequence of at least seven, more preferably at least nine, and most preferably between about 15 to about 30 amino acids. Antigenic epitopes are useful to raise antibodies, including monoclonal antibodies, that specifically bind the epitope. (See, for instance, Wilson et al., Cell 37:767–778 (1984); Sutcliffe, J. G. et al., Science 219:660–666 (1983).)

Similarly, immunogenic epitopes can be used to induce antibodies according to methods well known in the art. (See, for instance, Sutcliffe et al., supra; Wilson et al., supra; Chow, M. et al., Proc. Natl. Acad. Sci. USA 82:910–914; and Bittle, F. J. et al., J. Gen. Virol. 66:2347–2354 (1985).) A preferred immunogenic epitope includes the complete protein. The immunogenic epitopes may be presented together with a carrier protein, such as an albumin, to an animal system (such as rabbit or mouse) or, if it is long enough (at least about 25 amino acids), without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting.)

As used herein, the term "antibody" (Ab) or "monoclonal antibody" (Mab) is meant to include intact molecules as well as antibody fragments (such as, for example, Fab and F(ab')2 fragments) which are capable of specifically binding to protein. Fab and F(ab')2 fragments lack the Fc fragment of intact antibody, clear more rapidly from the circulation, and may have less non-specific tissue binding than an intact antibody. (Wahl et al., J. Nucl. Med. 24:316–325 (1983).) Thus, these fragments are preferred, as well as the products of a FAB or other immunoglobulin expression library. Moreover, antibodies of the present invention include chimeric, single chain, and humanized antibodies.

Fusion Proteins

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because secreted proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Also, peptide moieties may be added to the polypeptide to facilitate purification. Such regions may be removed prior to final preparation of the polypeptide. The addition of peptide moieties to facilitate handling of polypeptides are familiar and routine techniques in the art.

Moreover, polypeptides of the present invention, including fragments, and specifically epitopes, can be combined with parts of the constant domain of immunoglobulins (IgG), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331:84–86 (1988).) Fusion proteins having disulfide-linked dimeric structures (due to the IgG) can also be more efficient in binding and neutralizing other molecules, than the monomeric protein or protein fragment alone. (Fountoulakis et al., J. Biochem. 270:3958–3964 (1995).)

Similarly, EP-A-O 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52–58 (1995); K. Johanson et al., J. Biol. Chem. 270:9459–9471 (1995).)

Moreover, the polypeptides of the present invention can be fused to marker sequences, such as a peptide which facilitates purification of the fused polypeptide. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984).)

Thus, any of these above fusions can be engineered using the polynucleotides or the polypeptides of the present invention.

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the E. coli lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells; insect cells such as Drosophila S2 and Spodoptera Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the-N-terminal methionine is covalently linked.

Uses of the Polynucleotides

Each of the polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymorphisms), are presently available. Each polynucleotide of the present invention can be used as a chromosome marker.

Briefly, sequences can be mapped to chromosomes by preparing PCR primers (preferably 15–25 bp) from the sequences shown in SEQ ID NO:X. Primers can be selected using computer analysis so that primers do not span more than one predicted exon in the genomic DNA. These primers are then used for PCR screening of somatic cell hybrids containing individual human chromosomes. Only those hybrids containing the human gene corresponding to the SEQ ID NO:X will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the polynucleotides can also be achieved using fluorescence in situ hybridization (FISH) of a metaphase chromosomal spread. This technique uses polynucleotides as short as 500 or 600 bases; however, polynucleotides 2,000–4,000 bp are preferred. For a review of this technique, see Verma et al., "Human Chromosomes: a Manual of Basic Techniques," Pergamon Press, New York (1988).

For chromosome mapping, the polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. (Disease mapping data are found, for example, in V. McKusick, Mendelian Inheritance in Man (available on line through Johns Hopkins University Welch Medical Library) .) Assuming 1 megabase mapping resolution and one gene per 20 kb, a cDNA precisely localized to a chromosomal region associated with the disease could be one of 50–500 potential causative genes.

Thus, once coinheritance is established, differences in the polynucleotide and the corresponding gene between affected and unaffected individuals can be examined. First, visible structural alterations in the chromosomes, such as deletions or translocations, are examined in chromosome spreads or by PCR. If no structural alterations exist, the presence of point mutations are ascertained. Mutations observed in some or all affected individuals, but not in normal individuals, indicates that the mutation may cause the disease. However, complete sequencing of the polypeptide and the corresponding gene from several normal individuals is required to distinguish the mutation from a polymorphism. If a new polymorphism is identified, this polymorphic polypeptide can be used for further linkage analysis.

Furthermore, increased or decreased expression of the gene in affected individuals as compared to unaffected individuals can be assessed using polynucleotides of the present invention. Any of these alterations (altered expression, chromosomal rearrangement, or mutation) can be used as a diagnostic or prognostic marker.

In addition to the foregoing, a polynucleotide can be used to control gene expression through triple helix formation or antisense DNA or RNA. Both methods rely on binding of the polynucleotide to DNA or RNA. For these techniques, preferred polynucleotides are usually 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991) ) or to the mRNA itself (antisense—Okano, J. Neurochem. 56:560 (1991); Oligodeoxy-nucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat disease.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell.

The polynucleotides are also useful for identifying individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be used as additional DNA markers for RFLP.

The polynucleotides of the present invention can also be used as an alternative to RFLP, by determining the actual base-by-base DNA sequence of selected portions of an individual's genome. These sequences can be used to prepare PCR primers for amplifying and isolating such selected DNA, which can then be sequenced. Using this technique, individuals can be identified because each individual will have a unique set of DNA sequences. Once an unique ID database is established for an individual, positive identification of that individual, living or dead, can be made from extremely small tissue samples.

Forensic biology also benefits from using DNA-based identification techniques as disclosed herein. DNA sequences taken from very small biological samples such as tissues, e.g., hair or skin, or body fluids, e.g., blood, saliva, semen, etc., can be amplified using PCR. In one prior art technique, gene sequences amplified from polymorphic loci, such as DQa class II HLA gene, are used in forensic biology to identify individuals. (Erlich, H., PCR Technology, Freeman and Co. (1992).) Once these specific polymorphic loci are amplified, they are digested with one or more restriction enzymes, yielding an identifying set of bands on a Southern blot probed with DNA corresponding to the DQa class II HLA gene. Similarly, polynucleotides of the present invention can be used as polymorphic markers for forensic purposes.

There is also a need for reagents capable of identifying the source of a particular tissue. Such need arises, for example, in forensics when presented with tissue of unknown origin. Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination.

In the very least, the polynucleotides of the present invention can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of the Polypeptides

Each of the polypeptides identified herein can be used in numerous ways. The following description should be considered exemplary and utilizes known techniques.

A polypeptide of the present invention can be used to assay protein levels in a biological sample using antibody-based techniques. For example, protein expression in tissues can be studied with classical immunohistological methods. (Jalkanen, M., et al., J. Cell. Biol. 101:976–985 (1985); Jalkanen, M., et al., J. Cell . Biol. 105:3087–3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine (125I, 121I), carbon (14C), sulfur (35S), tritium (3H), indium (112In), and technetium (99mTc), and fluorescent labels, such as fluorescein and rhodamine, and biotin.

In addition to assaying protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 112In, 99mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).)

Thus, the invention provides a diagnostic method of a disorder, which involves (a) assaying the expression of a polypeptide of the present invention in cells or body fluid of an individual; (b) comparing the level of gene expression with a standard gene expression level, whereby an increase or decrease in the assayed polypeptide gene expression level compared to the standard expression level is indicative of a disorder.

Moreover, polypeptides of the present invention can be used to treat disease. For example, patients can be administered a polypeptide of the present invention in an effort to replace absent or decreased levels of the polypeptide (e.g., insulin), to supplement absent or decreased levels of a different polypeptide (e.g., hemoglobin S for hemoglobin B), to inhibit the activity of a polypeptide (e.g., an oncogene), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth).

Similarly, antibodies directed to a polypeptide of the present invention can also be used to treat disease. For example, administration of an antibody directed to a polypeptide of the present invention can bind and reduce overproduction of the polypeptide. Similarly, administration of an antibody can activate the polypeptide, such as by binding to a polypeptide bound to a membrane (receptor).

At the very least, the polypeptides of the present invention can be used as molecular weight markers on SDS-PAGE gels or on molecular sieve gel filtration columns using methods well known to those of skill in the art. Polypeptides can also be used to raise antibodies, which in turn are used to measure protein expression from a recombinant cell, as a way of assessing transformation of the host cell. Moreover, the polypeptides of the present invention can be used to test the following biological activities.

Biological Activities

The polynucleotides and polypeptides of the present invention can be used in assays to test for one or more biological activities. If these polynucleotides and polypeptides do exhibit activity in a particular assay, it is likely that these molecules may be involved in the diseases associated with the biological activity. Thus, the polynucleotides and polypeptides could be used to treat the associated disease.

Immune Activity

A polypeptide or polynucleotide of the present invention may be useful in treating deficiencies or disorders of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g., by chemotherapy or toxins), or infectious. Moreover, a polynucleotide or polypeptide of the present invention can be used as a marker or detector of a particular immune system disease or disorder.

A polynucleotide or polypeptide of the present invention may be useful in treating or detecting deficiencies or disorders of hematopoietic cells. A polypeptide or polynucleotide of the present invention could be used to increase differentiation and proliferation of hematopoietic cells, including the pluripotent stem cells, in an effort to treat those disorders associated with a decrease in certain (or many) types hematopoietic cells. Examples of immunologic deficiency syndromes include, but are not limited to: blood protein disorders (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, a polypeptide or polynucleotide of the present invention could also be used to modulate hemostatic (the stopping of bleeding) or thrombolytic activity (clot formation). For example, by increasing hemostatic or thrombolytic activity, a polynucleotide or polypeptide of the present invention could be used to treat blood coagulation disorders (e.g., afibrinogenemia, factor deficiencies), blood platelet disorders (e.g. thrombocytopenia), or wounds resulting from trauma, surgery, or other causes. Alternatively, a polynucleotide or polypeptide of the present invention that can decrease hemostatic or thrombolytic activity could be used to inhibit or dissolve clotting. These molecules could be important in the treatment of heart attacks (infarction), strokes, or scarring.

A polynucleotide or polypeptide of the present invention may also be useful in treating or detecting autoimmune disorders. Many autoimmune disorders result from inappropriate recognition of self as foreign material by immune cells. This inappropriate recognition results in an immune response leading to the destruction of the host tissue. Therefore, the administration of a polypeptide or polynucleotide of the present invention that inhibits an immune response, particularly the proliferation, differentiation, or chemotaxis of T-cells, may be an effective therapy in preventing autoimmune disorders.

Examples of autoimmune disorders that can be treated or detected by the present invention include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitus, and autoimmune inflammatory eye disease.

Similarly, allergic reactions and conditions, such as asthma (particularly allergic asthma) or other respiratory problems, may also be treated by a polypeptide or polynucleotide of the present invention. Moreover, these molecules can be used to treat anaphylaxis, hypersensitivity to an antigenic molecule, or blood group incompatibility.

A polynucleotide or polypeptide of the present invention may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of a polypeptide or polynucleotide of the present invention that inhibits an immune response, particularly the proliferation, differentiation, or chemotaxis of T-cells, may be an effective therapy in preventing organ rejection or GVHD.

Similarly, a polypeptide or polynucleotide of the present invention may also be used to modulate inflammation. For example, the polypeptide or polynucleotide may inhibit the proliferation and differentiation of cells involved in an inflammatory response. These molecules can be used to treat inflammatory conditions, both chronic and acute conditions, including inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

A polypeptide or polynucleotide can be used to treat or detect hyperproliferative disorders, including neoplasms. A polypeptide or polynucleotide of the present invention may inhibit the proliferation of the disorder through direct or indirect interactions. Alternatively, a polypeptide or polynucleotide of the present invention may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as a chemotherapeutic agent.

Examples of hyperproliferative disorders that can be treated or detected by a polynucleotide or polypeptide of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated or detected by a polynucleotide or polypeptide of the present invention. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

Infectious Disease

A polypeptide or polynucleotide of the present invention can be used to treat or detect infectious agents. For example, by increasing the immune response, particularly increasing the proliferation and differentiation of B and/or T cells, infectious diseases may be treated. The immune response may be increased by either enhancing an existing immune response, or by initiating a new immune response. Alternatively, the polypeptide or polynucleotide of the present invention may also directly inhibit the infectious agent, without necessarily eliciting an immune response.

Viruses are one example of an infectious agent that can cause disease or symptoms that can be treated or detected by a polynucleotide or polypeptide of the present invention. Examples of viruses, include, but are not limited to the following DNA and RNA viral families: Arbovirus, Adenoviridae, Arenaviridae, Arterivirus, Birnaviridae, Bunyaviridae, Caliciviridae, Circoviridae, Coronaviridae, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza), Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, encephalitis, eye infections (e.g., conjunctivitis, keratitis), chronic fatigue syndrome, hepatitis (A, B, C, E, Chronic Active, Delta), meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. A polypeptide or polynucleotide of the present invention can be used to treat or detect any of these symptoms or diseases.

Similarly, bacterial or fungal agents that can cause disease or symptoms and that can be treated or detected by a polynucleotide or polypeptide of the present invention include, but not limited to, the following Gram-Negative and Gram-positive bacterial families and fungi: Actinomycetales (e.g., Corynebacterium, Mycobacterium, Norcardia), Aspergillosis, Bacillaceae (e.g., Anthrax, Clostridium), Bacteroidaceae, Blastomycosis, Bordetella, Borrelia, Brucellosis, Candidiasis, Campylobacter, Coccidioidomycosis, Cryptococcosis, Dermatocycoses, Enterobacteriaceae (Klebsiella, Salmonella, Serratia, Yersinia), Erysipelothrix, Helicobacter, Legionellosis, Leptospirosis, Listeria, Mycoplasmatales, Neisseriaceae (e.g., Acinetobacter, Gonorrhea, Menigococcal), Pasteurellacea Infections (e.g., Actinobacillus, Heamophilus, Pasteurella), Pseudomonas, Rickettsiaceae, Chlamydiaceae, Syphilis, and Staphylococcal. These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. A polypeptide or polynucleotide of the present invention can be used to treat or detect any of these symptoms or diseases.

Moreover, parasitic agents causing disease or symptoms that can be treated or detected by a polynucleotide or polypeptide of the present invention include, but not limited to, the following families: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas. These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), Malaria, pregnancy complications, and toxoplasmosis. A polypeptide or polynucleotide of the present invention can be used to treat or detect any of these symptoms or diseases.

Preferably, treatment using a polypeptide or polynucleotide of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Regeneration

A polynucleotide or polypeptide of the present invention can be used to differentiate, proliferate, and attract cells, leading to the regeneration of tissues. (See, Science 276:59–87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vascular (including vascular endothelium), nervous, hematopoietic, and skeletal (bone, cartilage, tendon, and ligament) tissue. Preferably, regeneration occurs without or decreased scarring. Regeneration also may include angiogenesis.

Moreover, a polynucleotide or polypeptide of the present invention may increase regeneration of tissues difficult to heal. For example, increased tendon/ligament regeneration would quicken recovery time after damage. A polynucleotide or polypeptide of the present invention could also be used prophylactically in an effort to avoid damage. Specific diseases that could be treated include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using a polynucleotide or polypeptide of the present invention to proliferate and differentiate nerve cells. Diseases that could be treated using this method include central and peripheral nervous system diseases, neuropathies, or mechanical and traumatic disorders (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated using the polynucleotide or polypeptide of the present invention.

Chemotaxis

A polynucleotide or polypeptide of the present invention may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

A polynucleotide or polypeptide of the present invention may increase chemotaxic activity of particular cells. These chemotactic molecules can then be used to treat inflammation, infection, hyperproliferative disorders, or any immune system disorder by increasing the number of cells targeted to a particular location in the body. For example, chemotaxic molecules can be used to treat wounds and other trauma to tissues by attracting immune cells to the injured location. Chemotactic molecules of the present invention can also attract fibroblasts, which can be used to treat wounds.

It is also contemplated that a polynucleotide or polypeptide of the present invention may inhibit chemotactic activity. These molecules could also be used to treat disorders. Thus, a polynucleotide or polypeptide of the present invention could be used as an inhibitor of chemotaxis.

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors), or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2):Chapter 5 (1991).) Similarly, the molecule can be closely related to the natural receptor to which the polypeptide binds, or at least, a fragment of the receptor capable of being bound by the polypeptide (e.g., active site). In either case, the molecule can be rationally designed using known techniques.

Preferably, the screening for these molecules involves producing appropriate cells which express the polypeptide, either as a secreted protein or on the cell membrane. Preferred cells include cells from mammals, yeast, Drosophila, or *E. coli*. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

All of these above assays can be used as diagnostic or prognostic markers. The molecules discovered using these assays can be used to treat disease or to bring about a particular result in a patient (e.g., blood vessel growth) by activating or inhibiting the polypeptide/molecule. Moreover, the assays can discover agents which may inhibit or enhance the production of the polypeptide from suitably manipulated cells or tissues.

Therefore, the invention includes a method of identifying compounds which bind to a polypeptide of the invention comprising the steps of: (a) incubating a candidate binding compound with a polypeptide of the invention; and (b) determining if binding has occurred. Moreover, the invention includes a method of identifying agonists/antagonists comprising the steps of: (a) incubating a candidate compound with a polypeptide of the invention, (b) assaying a biological activity , and (b) determining if a biological activity of the polypeptide has been altered.

Other Activities

A polypeptide or polynucleotide of the present invention may also increase or decrease the differentiation or proliferation of embryonic stem cells, besides, as discussed above, hematopoietic lineage.

A polypeptide or polynucleotide of the present invention may also be used to modulate mammalian characteristics, such as body height, weight, hair color, eye color, skin, percentage of adipose tissue, pigmentation, size, and shape (e.g., cosmetic surgery). Similarly, a polypeptide or polynucleotide of the present invention may be used to modulate mammalian metabolism affecting catabolism, anabolism, processing, utilization, and storage of energy.

A polypeptide or polynucleotide of the present invention may be used to change a mammal's mental state or physical state by influencing biorhythms, caricadic rhythms, depression (including depressive disorders), tendency for violence, tolerance for pain, reproductive capabilities (preferably by Activin or Inhibin-like activity), hormonal or endocrine levels, appetite, libido, memory, stress, or other cognitive qualities.

A polypeptide or polynucleotide of the present invention may also be used as a food additive or preservative, such as to increase or decrease storage capabilities, fat content, lipid, protein, carbohydrate, vitamins, minerals, cofactors or other nutritional components.

Other Preferred Embodiments

Other preferred embodiments of the claimed invention include an isolated nucleic acid molecule comprising a nucleotide sequence which is at least 95% identical to a sequence of at least about 50 contiguous nucleotides in the nucleotide sequence of SEQ ID NO:X wherein X is any integer as defined in Table 1.

Also preferred is a nucleic acid molecule wherein said sequence of contiguous nucleotides is included in the nucleotide sequence of SEQ ID NO:X in the range of positions beginning with the nucleotide at about the position of the 5' Nucleotide of the Clone Sequence and ending with the nucleotide at about the position of the 3' Nucleotide of the Clone Sequence as defined for SEQ ID NO:X in Table 1.

Also preferred is a nucleic acid molecule wherein said sequence of contiguous nucleotides is included in the nucleotide sequence of SEQ ID NO:X in the range of positions beginning with the nucleotide at about the position of the 5' Nucleotide of the Start Codon and ending with the nucleotide at about the position of the 3' Nucleotide of the Clone Sequence as defined for SEQ ID NO:X in Table 1.

Similarly preferred is a nucleic acid molecule wherein said sequence of contiguous nucleotides is included in the nucleotide sequence of SEQ ID NO:X in the range of positions beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in Table 1.

Also preferred is an isolated nucleic acid molecule comprising a nucleotide sequence which is at least 95% identical to a sequence of at least about 150 contiguous nucleotides in the nucleotide sequence of SEQ ID NO:X.

Further preferred is an isolated nucleic acid molecule comprising a nucleotide sequence which is at least 95% identical to a sequence of at least about 500 contiguous nucleotides in the nucleotide sequence of SEQ ID NO:X.

A further preferred embodiment is a nucleic acid molecule comprising a nucleotide sequence which is at least 95% identical to the nucleotide sequence of SEQ ID NO:X beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in Table 1.

A further preferred embodiment is an isolated nucleic acid molecule comprising a nucleotide sequence which is at least 95% identical to the complete nucleotide sequence of SEQ ID NO:X.

Also preferred is an isolated nucleic acid molecule which hybridizes under stringent hybridization conditions to a nucleic acid molecule, wherein said nucleic acid molecule which hybridizes does not hybridize under stringent hybridization conditions to a nucleic acid molecule having a nucleotide sequence consisting of only A residues or of only T residues.

Also preferred is a composition of matter comprising a DNA molecule which comprises a human cDNA clone identified by a cDNA Clone Identifier in Table 1, which DNA molecule is contained in the material deposited with the American Type Culture Collection and given the ATCC Deposit Number shown in Table 1 for said cDNA Clone Identifier.

Also preferred is an isolated nucleic acid molecule comprising a nucleotide sequence which is at least 95% identical to a sequence of at least 50 contiguous nucleotides in the nucleotide sequence of a human cDNA clone identified by a cDNA Clone Identifier in Table 1, which DNA molecule is contained in the deposit given the ATCC Deposit Number shown in Table 1.

Also preferred is an isolated nucleic acid molecule, wherein said sequence of at least 50 contiguous nucleotides is included in the nucleotide sequence of the complete open reading frame sequence encoded by said human cDNA clone.

Also preferred is an isolated nucleic acid molecule comprising a nucleotide sequence which is at least 95% identical to sequence of at least 150 contiguous nucleotides in the nucleotide sequence encoded by said human cDNA clone.

A further preferred embodiment is an isolated nucleic acid molecule comprising a nucleotide sequence which is at least 95% identical to sequence of at least 500 contiguous nucleotides in the nucleotide sequence encoded by said human cDNA clone.

A further preferred embodiment is an isolated nucleic acid molecule comprising a nucleotide sequence which is at least 95% identical to the complete nucleotide sequence encoded by said human cDNA clone.

A further preferred embodiment is a method for detecting in a biological sample a nucleic acid molecule comprising a nucleotide sequence which is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1; which method comprises a step of comparing a nucleotide sequence of at least one nucleic acid molecule in said sample with a sequence selected from said group and determining whether the sequence of said nucleic acid molecule in said sample is at least 95% identical to said selected sequence.

Also preferred is the above method wherein said step of comparing sequences comprises determining the extent of nucleic acid hybridization between nucleic acid molecules in said sample and a nucleic acid molecule comprising said sequence selected from said group. Similarly, also preferred is the above method wherein said step of comparing sequences is performed by comparing the nucleotide sequence determined from a nucleic acid molecule in said sample with said sequence selected from said group. The nucleic acid molecules can comprise DNA molecules or RNA molecules.

A further preferred embodiment is a method for identifying the species, tissue or cell type of a biological sample which method comprises a step of detecting nucleic acid molecules in said sample, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1.

The method for identifying the species, tissue or cell type of a biological sample can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a method for diagnosing in a subject a pathological condition associated with abnormal structure or expression of a gene encoding a protein identified in Table 1, which method comprises a step of detecting in a biological sample obtained from said subject nucleic acid molecules, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1.

The method for diagnosing a pathological condition can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a composition of matter comprising isolated nucleic acid molecules wherein the nucleotide sequences of said nucleic acid molecules comprise a panel of at least two nucleotide sequences, wherein at least one sequence in said panel is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1. The nucleic acid molecules can comprise DNA molecules or RNA molecules.

Also preferred is an isolated polypeptide comprising an amino acid sequence at least 90% identical to a sequence of at least about 10 contiguous amino acids in the amino acid sequence of SEQ ID NO:Y wherein Y is any integer as defined in Table 1.

Also preferred is a polypeptide, wherein said sequence of contiguous amino acids is included in the amino acid sequence of SEQ ID NO:Y in the range of positions beginning with the residue at about the position of the First Amino Acid of the Secreted Portion and ending with the residue at about the Last Amino Acid of the Open Reading Frame as set forth for SEQ ID NO:Y in Table 1.

Also preferred is an isolated polypeptide comprising an amino acid sequence at least 95% identical to a sequence of at least about 30 contiguous amino acids in the amino acid sequence of SEQ ID NO:Y.

Further preferred is an isolated polypeptide comprising an amino acid sequence at least 95% identical to a sequence of at least about 100 contiguous amino acids in the amino acid sequence of SEQ ID NO:Y.

Further preferred is an isolated polypeptide comprising an amino acid sequence at least 95% identical to the complete amino acid sequence of SEQ ID NO:Y.

Further preferred is an isolated polypeptide comprising an amino acid sequence at least 90% identical to a sequence of at least about 10 contiguous amino acids in the complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is a polypeptide wherein said sequence of contiguous amino acids is included in the amino acid sequence of a secreted portion of the complete protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to a sequence of at least about 30 contiguous amino acids in the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to a sequence of at least about 100 contiguous amino acids in the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Further preferred is an isolated antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1.

Further preferred is a method for detecting in a biological sample a polypeptide comprising an amino acid sequence which is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1; which method comprises a step of comparing an amino acid sequence of at least one polypeptide molecule in said sample with a sequence selected from said group and determining whether the sequence of said polypeptide molecule in said sample is at least 90% identical to said sequence of at least 10 contiguous amino acids.

Also preferred is the above method wherein said step of comparing an amino acid sequence of at least one polypeptide molecule in said sample with a sequence selected from said group comprises determining the extent of specific binding of polypeptides in said sample to an antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1.

Also preferred is the above method wherein said step of comparing sequences is performed by comparing the amino acid sequence determined from a polypeptide molecule in said sample with said sequence selected from said group.

Also preferred is a method for identifying the species, tissue or cell type of a biological sample which method comprises a step of detecting polypeptide molecules in said sample, if any, comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1.

Also preferred is the above method for identifying the species, tissue or cell type of a biological sample, which method comprises a step of detecting polypeptide molecules comprising an amino acid sequence in a panel of at least two amino acid sequences, wherein at least one sequence in said panel is at least 90% identical to a sequence of at least 10 contiguous amino acids in a sequence selected from the above group.

Also preferred is a method for diagnosing in a subject a pathological condition associated with abnormal structure or expression of a gene encoding a protein identified in Table 1, which method comprises a step of detecting in a biological sample obtained from said subject polypeptide molecules comprising an amino acid sequence in a panel of at least two amino acid sequences, wherein at least one sequence in said panel is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1.

In any of these methods, the step of detecting said polypeptide molecules includes using an antibody.

Also preferred is an isolated nucleic acid molecule comprising a nucleotide sequence which is at least 95% identical to a nucleotide sequence encoding a polypeptide wherein said polypeptide comprises an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1.

Also preferred is an isolated nucleic acid molecule, wherein said nucleotide sequence encoding a polypeptide has been optimized for expression of said polypeptide in a prokaryotic host.

Also preferred is an isolated nucleic acid molecule, wherein said polypeptide comprises an amino acid sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1.

Further preferred is a method of making a recombinant vector comprising inserting any of the above isolated nucleic acid molecule into a vector. Also preferred is the recombinant vector produced by this method. Also preferred is a method of making a recombinant host cell comprising introducing the vector into a host cell, as well as the recombinant host cell produced by this method.

Also preferred is a method of making an isolated polypeptide comprising culturing this recombinant host cell under conditions such that said polypeptide is expressed and recovering said polypeptide. Also preferred is this method of making an isolated polypeptide, wherein said recombinant host cell is a eukaryotic cell and said polypeptide is a secreted portion of a human protein comprising an amino acid sequence selected from the group consisting of: an amino acid sequence of SEQ ID NO:Y beginning with the residue at the position of the First Amino Acid of the Secreted Portion of SEQ ID NO:Y wherein Y is an integer set forth in Table 1 and said position of the First Amino Acid of the Secreted Portion of SEQ ID NO:Y is defined in Table 1; and an amino acid sequence of a secreted portion of a protein encoded by a human cDNA clone identified by a cDNA Clone Identifier in Table 1 and contained in the deposit with the ATCC Deposit Number shown for said cDNA clone in Table 1. The isolated polypeptide produced by this method is also preferred.

Also preferred is a method of treatment of an individual in need of an increased level of protein activity, which method comprises administering to such an individual a pharmaceutical composition comprising an amount of an isolated polypeptide, polynucleotide, or antibody of the claimed invention effective to increase the level of said protein activity in said individual.

Having generally described the invention, the same will be more readily understood by reference to the following examples, which are provided by way of illustration and are not intended as limiting.

EXAMPLES

Example 1

Isolation of a Selected cDNA Clone from the Deposited Sample

Each cDNA clone in a cited ATCC deposit is contained in a plasmid vector. Table 1 identifies the vectors used to construct the cDNA library from which each clone was isolated. In many cases, the vector used to construct the library is a phage vector from which a plasmid has been excised. The table immediately below correlates the related plasmid for each phage vector used in constructing the cDNA library. For example, where a particular clone is identified in Table 1 as being isolated in the vector "Lambda Zap," the corresponding deposited clone is in "pBluescript."

| Vector Used to Construct Library | Corresponding Deposited Plasmid |
|---|---|
| Lambda Zap | pBluescript (pBS) |
| Uni-Zap XR | pBluescript (pBS) |
| Zap Express | pBK |
| lafmid BA | plafmid BA |
| pSport1 | pSport1 |
| pCMVSport 2.0 | pCMVSport 2.0 |
| pCMVSport 3.0 | pCMVSport 3.0 |
| pCR ® 2.1 | pCR ® 2.1 |

Vectors Lambda Zap (U.S. Pat. Nos. 5,128,256 and 5,286, 636), Uni-Zap XR (U.S. Pat. Nos. 5,128, 256 and 5,286, 636), Zap Express (U.S. Pat. Nos. 5,128,256 and 5,286,636), pBluescript (pBS) (Short, J. M. et al., Nucleic Acids Res. 16:7583–7600 (1988); Alting-Mees, M. A. and Short, J. M., Nucleic Acids Res. 17:9494 (1989)) and pBK (Alting-Mees, M. A. et al., Strategies 5:58–61 (1992)) are commercially available from Stratagene Cloning Systems, Inc., 11011 N. Torrey Pines Road, La Jolla, Calif., 92037. pBS contains an ampicillin resistance gene and pBK contains a neomycin resistance gene. Both can be transformed into E. coli strain XL-1 Blue, also available from Stratagene. pBS comes in 4 forms SK+, SK−, KS+ and KS. The S and K refers to the orientation of the polylinker to the T7 and T3 primer sequences which flank the polylinker region ("S" is for SacI and "K" is for KpnI which are the first sites on each respective end of the linker). "+" or "−" refer to the orientation of the f1 origin of replication ("ori"), such that in one orientation, single stranded rescue initiated from the f1 ori generates sense strand DNA and in the other, antisense.

Vectors pSport1, pCMVSport 2.0 and pCMVSport 3.0, were obtained from Life Technologies, Inc., P. O. Box 6009, Gaithersburg, Md. 20897. All Sport vectors contain an ampicillin resistance gene and may be transformed into E. coli strain DH10B, also available from Life Technologies. (See, for instance, Gruber, C. E., et al., Focus 15:59 (1993).) Vector lafmid BA (Bento Soares, Columbia University, NY) contains an ampicillin resistance gene and can be transformed into E. coli strain XL-1 Blue. Vector pCR®2.1, which is available from Invitrogen, 1600 Faraday Avenue, Carlsbad, Calif. 92008, contains an ampicillin resistance gene and may be transformed into E. coli strain DH10B, available from Life Technologies. (See, for instance, Clark, J. M., Nuc. Acids Res. 16:9677–9686 (1988) and Mead, D. et al., Bio/Technology 9: (1991).) Preferably, a polynucleotide of the present invention does not comprise the phage vector sequences identified for the particular clone in Table 1, as well as the corresponding plasmid vector sequences designated above.

The deposited material in the sample assigned the ATCC Deposit Number cited in Table 1 for any given cDNA clone also may contain one or more additional plasmids, each comprising a cDNA clone different from that given clone. Thus, deposits sharing the same ATCC Deposit Number contain at least a plasmid for each cDNA clone identified in Table 1. Typically, each ATCC deposit sample cited in Table 1 comprises a mixture of approximately equal amounts (by weight) of about 50 plasmid DNAs, each containing a different cDNA clone; but such a deposit sample may include plasmids for more or less than 50 cDNA clones, up to about 500 cDNA clones.

Two approaches can be used to isolate a particular clone from the deposited sample of plasmid DNAs cited for that clone in Table 1. First, a plasmid is directly isolated by screening the clones using a polynucleotide probe corresponding to SEQ ID NO:X.

Particularly, a specific polynucleotide with 30–40 nucleotides is synthesized using an Applied Biosystems DNA synthesizer according to the sequence reported. The oligonucleotide is labeled, for instance, with $^{32}P$-γ-ATP using T4 polynucleotide kinase and purified according to routine methods. (E.g., Maniatis et al., Molecular Cloning: A Laboratory Manual, Cold Spring Harbor Press, Cold Spring, N.Y. (1982).) The plasmid mixture is transformed into a suitable host, as indicated above (such as XL-1 Blue (Stratagene)) using techniques known to those of skill in the art, such as those provided by the vector supplier or in related publications or patents cited above. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other techniques known to those of skill in the art.

Alternatively, two primers of 17–20 nucleotides derived from both ends of the SEQ ID NO:X (i.e., within the region of SEQ ID NO:X bounded by the 5' NT and the 3' NT of the clone defined in Table 1) are synthesized and used to amplify the desired cDNA using the deposited cDNA plasmid as a template. The polymerase chain reaction is carried out under routine conditions, for instance, in 25 μl of reaction mixture with 0.5 ug of the above cDNA template. A convenient reaction mixture is 1.5–5 mM $MgCl_2$, 0.01% (w/v) gelatin, 20 μM each of dATP, dCTP, dGTP, dTTP, 25 pmol of each primer and 0.25 Unit of Taq polymerase. Thirty five cycles of PCR (denaturation at 94° C. for 1 min; annealing at 55° C. for 1 min; elongation at 72° C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Several methods are available for the identification of the 5' or 3' non-coding portions of a gene which may not be present in the deposited clone. These methods include but are not limited to, filter probing, clone enrichment using specific probes, and protocols similar or identical to 5' and 3' "RACE" protocols which are well known in the art. For instance, a method similar to 5' RACE is available for generating the missing 5' end of a desired full-length transcript. (Fromont-Racine et al., Nucleic Acids Res. 21(7): 1683–1684 (1993).) Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product may then be sequenced and used to generate the full length gene.

This above method starts with total RNA isolated from the desired source, although poly-A+ RNA can be used. The RNA preparation can then be treated with phosphatase if necessary to eliminate 5' phosphate groups on degraded or damaged RNA which may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the desired gene.

Example 2

Isolation of Genomic Clones Corresponding to a Polynucleotide

A human genomic PI library (Genomic Systems, Inc.) is screened by PCR using primers selected for the cDNA sequence corresponding to SEQ ID NO:X., according to the method described in Example 1. (See also, Sambrook.)

Example 3

Tissue Distribution of Polypeptide

Tissue distribution of mRNA expression of polynucleotides of the present invention is determined using protocols for Northern blot analysis, described by, among others, Sambrook et al. For example, a cDNA probe produced by the method described in Example 1 is labeled with $P^{32}$ using the rediprime™ DNA labeling system (Amersham Life Science), according to manufacturer's instructions. After labeling, the probe is purified using CHROMA SPIN-100™ column (Clontech Laboratories, Inc.), according to manufacturer's protocol number PT1200-1. The purified labeled probe is then used to examine various human tissues for mRNA expression.

Multiple Tissue Northern (MTN) blots containing various human tissues (H) or human immune system tissues (IM) (Clontech) are examined with the labeled probe using ExpressHyb™ hybridization solution (Clontech) according to manufacturer's protocol number PT1190-1. Following hybridization and washing, the blots are mounted and exposed to film at −70° C. overnight, and the films developed according to standard procedures.

Example 4

Chromosomal Mapping of the Polynucleotides

An oligonucleotide primer set is designed according to the sequence at the 5' end of SEQ ID NO:X. This primer preferably spans about 100 nucleotides. This primer set is then used in a polymerase chain reaction under the following set of conditions: 30 seconds, 95° C.; 1 minute, 56° C.; 1 minute, 70° C. This cycle is repeated 32 times followed by one 5 minute cycle at 70° C. Human, mouse, and hamster DNA is used as template in addition to a somatic cell hybrid panel containing individual chromosomes or chromosome fragments (Bios, Inc). The reactions is analyzed on either 8% polyacrylamide gels or 3.5% agarose gels. Chromosome mapping is determined by the presence of an approximately 100 bp PCR fragment in the particular somatic cell hybrid.

Example 5

Bacterial Expression of a Polypeptide

A polynucleotide encoding a polypeptide of the present invention is amplified using PCR oligonucleotide primers corresponding to the 5' and 3' ends of the DNA sequence, as outlined in Example 1, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance (Amp$^r$), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the E. coli strain M15/rep4 (Qiagen, Inc.) which contains multiple copies of the plasmid pREP4, which expresses the lacI repressor and also confers kanamycin resistance (Kan$^r$). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG (Isopropyl-B-D-thiogalacto pyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 6000×g). The cell pellet is solubilized in the chaotropic agent 6 Molar Guanidine HCl by stirring for 3–4 hours at 4° C. The cell debris is removed by centrifugation, and the supernatant containing the polypeptide is loaded onto a nickel-nitrilo-tri-acetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM immidazole. Immidazole is removed by a final dialyzing step against PBS or 50 mM sodium acetate pH 6 buffer plus 200 mM NaCl. The purified protein is stored at 4° C. or frozen at −80° C.

In addition to the above expression vector, the present invention further includes an expression vector comprising phage operator and promoter elements operatively linked to a polynucleotide of the present invention, called pHE4a. (ATCC Accession Number 209645, deposited on Feb. 25, 1998.) This vector contains: 1) a neomycinphosphotransferase gene as a selection marker, 2) an E. coli origin of replication, 3) a T5 phage promoter sequence, 4) two lac operator sequences, 5) a Shine-Delgarno sequence, and 6) the lactose operon repressor gene (lacIq). The origin of replication (oriC) is derived from pUC19 (LTI, Gaithersburg, Md.). The promoter sequence and operator sequences are made synthetically.

DNA can be inserted into the pHEa by restricting the vector with NdeI and XbaI, BamHI, XhoI, or Asp718, running the restricted product on a gel, and isolating the larger fragment (the stuffer fragment should be about 310 base pairs). The DNA insert is generated according to the PCR protocol described in Example 1, using PCR primers having restriction sites for NdeI (5' primer) and XbaI, BamHI, XhoI, or Asp718 (3' primer). The PCR insert is gel purified and restricted with compatible enzymes. The insert and vector are ligated according to standard protocols.

The engineered vector could easily be substituted in the above protocol to express protein in a bacterial system.

Example 6

Purification of a Polypeptide from an Inclusion Body

The following alternative method can be used to purify a polypeptide expressed in E coli when it is present in the form of inclusion bodies. Unless otherwise specified, all of the following steps are conducted at 4–10° C.

Upon completion of the production phase of the E. coli fermentation, the cell culture is cooled to 4–10° C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the polypeptide containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded polypeptide solution, a previously prepared tangential filtration unit equipped with 0.16 μm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Commassie blue stained 16% SDS-PAGE gel when 5 μg of purified protein is loaded. The purified protein can also be tested for endotoxin/LPS contamination, and typically the LPS content is less than 0.1 ng/ml according to LAL assays.

Example 7

Cloning and Expression of a Polypeptide in a Baculovirus Expression System

In this example, the plasmid shuttle vector pA2 is used to insert a polynucleotide into a baculovirus to express a polypeptide. This expression vector contains the strong polyhedrin promoter of the Autographa californica nuclear polyhedrosis virus (AcMNPV) followed by convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from E. coli under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pAc373, pVL941, and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31–39 (1989).

Specifically, the cDNA sequence contained in the deposited clone, including the AUG initiation codon and the naturally associated leader sequence identified in Table 1, is amplified using the PCR protocol described in Example 1. If the naturally occurring signal sequence is used to produce the secreted protein, the pA2 vector does not need a second signal peptide. Alternatively, the vector can be modified (pA2 GP) to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five $\mu$g of a plasmid containing the polynucleotide is co-transfected with 1.0 $\mu$g of a commercially available linearized baculovirus DNA ("BaculoGold™ baculovirus DNA", Pharmingen, San Diego, Calif.), using the lipofection method described by Felgner et al., Proc. Natl. Acad. Sci. USA 84:7413–7417 (1987). One $\mu$g of BaculoGold™ virus DNA and 5 $\mu$g of the plasmid are mixed in a sterile well of a microtiter plate containing 50 $\mu$l of serum-free Grace's medium (Life Technologies Inc., Gaithersburg, Md.). Afterwards, 10 $\mu$l Lipofectin plus 90 $\mu$l Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added. Cultivation is then continued at 27° C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10.) After appropriate incubation, blue stained plaques are picked with the tip of a micropipettor (e.g., Eppendorf). The agar containing the recombinant viruses is then resuspended in a microcentrifuge tube containing 200 $\mu$l of Grace's medium and the suspension containing the recombinant baculovirus is used to infect Sf9 cells seeded in 35 mm dishes. Four days later the supernatants of these culture dishes are harvested and then they are stored at 4° C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 $\mu$Ci of $^{35}$S-methionine and 5 $\mu$Ci $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Example 8

Expression of a Polypeptide in Mammalian Cells

The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC 37152), pSV2dhfr (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. 253:1357–1370 (1978); Hamlin, J. L. and Ma, C., Biochem. et Biophys. Acta, 1097:107–143 (1990); Page, M. J. and Sydenham, M. A., Biotechnology 9:64–68 (1991).) Another useful selection marker is the enzyme glutamine synthase (GS) (Murphy et al., Biochem J. 227:277–279 (1991); Bebbington et al., Bio/Technology 10:169–175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

Derivatives of the plasmid pSV2-dhfr (ATCC Accession No. 37146), the expression vectors pC4 (ATCC Accession No. 209646) and pC6 (ATCC Accession No.209647) contain the strong promoter (LTR) of the Rous Sarcoma Virus (Cullen et al., Molecular and Cellular Biology, 438–447 (March, 1985)) plus a fragment of the CMV-enhancer (Boshart et al., Cell 41:521–530 (1985).) Multiple cloning sites, e.g., with the restriction enzyme cleavage sites BamHI, XbaI and Asp718, facilitate the cloning of the gene of interest. The vectors also contain the 3' intron, the polyadenylation and termination signal of the rat preproinsulin gene, and the mouse DHFR gene under control of the SV40 early promoter.

Specifically, the plasmid pC6, for example, is digested with appropriate restriction enzymes and then dephosphorylated using calf intestinal phosphates by procedures known in the art. The vector is then isolated from a 1% agarose gel.

A polynucleotide of the present invention is amplified according to the protocol outlined in Example 1. If the naturally occurring signal sequence is used to produce the secreted protein, the vector does not need a second signal peptide. Alternatively, if the naturally occurring signal sequence is not used, the vector can be modified to include a heterologous signal sequence. (See, e.g., WO 96/34891.)

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. E. coli HB101 or XL-1 Blue cells are then transformed and bacteria are identified that contain the fragment inserted into plasmid pC6 using, for instance, restriction enzyme analysis.

Chinese hamster ovary cells lacking an active DHFR gene is used for transfection. Five µg of the expression plasmid pC6 is cotransfected with 0.5 µg of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 µM, 2 µM, 5 µM, 10 mM, 20 mM). The same procedure is repeated until clones are obtained which grow at a concentration of 100–200 µM. Expression of the desired gene product is analyzed, for instance, by SDS-PAGE and Western blot or by reversed phase HPLC analysis.

Example 9

Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Example 5; see also EPA 394,827; Traunecker, et al., Nature 331:84–86 (1988).) Similarly, fusion to IgG-1, IgG-3, and albumin increases the halflife time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule, or the protocol described in Example 5.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector.

For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and a polynucleotide of the present invention, isolated by the PCR protocol described in Example 1, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

Human IgG Fc region:
GGGATCCGGAGCCCAAATCTTCTGA-
CAAAACTCACACATGCCCACCGTGC-
CCAGCACCTGAATTCGAGGGTGCACCGT-
CAGTCTTCCTCTTCCCCCCAAAACCCAAGGAC
ACCCTCATGATCTCCCGGACTCCTGAG-
GTCACATGCGTGGTGGTGGACGTAAGC-
CACGAAGACCCTGAGGTCAAGT-
TCAACTGGTACGTGGACGGCGTGGAGGTGCAT
AATGCCAAGACAAAGCCGCGGGAGGAG-
CAGTACAACAGCACGTACCGTGTGGT-
CAGCGTCCTCACCGTCCTGCACCAG-
GACTGGCTGAATGGCAAGGAGTACAAGTGCAA
GGTCTCCAACAAAGCCCTCCCAAC-
CCCCATCGAGAAAACCATCTCCAAAGC-
CAAAGGGCAGCCCCGAGAACCACAGGTG-
TACACCCTGCCCCCATCCCGGGATGAGCTGACC
AAGAACCAGGTCAGCCTGACCTGCCTG-
GTCAAAGGCTTCTATCCAAGCGA-
CATCGCCGTGGAGTGGGAGAG-
CAATGGGCAGCCGGAGAACAACTACAAGACC
ACGCCTCCCGTGCTGGACTCCGACG-
GCTCCTTCTTCCTCTACAGCAAGCTCAC-
CGTGGACAAGAGCAGGTGGCAGCAGGG-
GAACGTCTTCTCATGCTCCGTGATGCATGAGGC
TCTGCACAACCACTACACGCAGAAGAGC-
CTCTCCCTGTCTCCGGGTAAATGAGTGC-
GACGGCCGCGACTCTAGAGGAT (SEQ ID NO:13)

Example 10

Production of an Antibody from a Polypeptide

The antibodies of the present invention can be prepared by a variety of methods. (See, Current Protocols, Chapter 2.) For example, cells expressing a polypeptide of the present invention is administered to an animal to induce the production of sera containing polyclonal antibodies. In a preferred method, a preparation of the secreted protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Köhler et al., Nature 256:495 (1975); Köhler et al., Eur. J. Immunol. 6:511 (1976); Köhler et al., Eur. J. Immunol. 6:292 (1976); Hammerling et al., in: Monoclonal Antibodies and T-Cell Hybridomas, Elsevier, N.Y., pp. 563–681 (1981).) In general, such procedures involve immunizing an animal (preferably a mouse) with polypeptide or, more preferably, with a secreted polypeptide-expressing cell. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 µg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP20), available from the ATCC. After fusion, the resulting hybridoma cells are selectively maintained in HAT medium, and then cloned by limiting dilution as described by Wands et al. (Gastroenterology 80:225–232 (1981).) The hybridoma cells obtained through such a selection are then assayed to identify clones which secrete antibodies capable of binding the polypeptide.

Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, secreted protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Example 11

Method of Determining Alterations in a Gene Corresponding to a Polynucleotide

RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:X. Suggested PCR conditions consist of 35 cycles at 95° C. for 30 seconds; 60–120 seconds at 52–58° C.; and seconds at 70° C., using buffer solutions described in Sidransky, D., et al., Science 252:706 (1991).

PCR products are then sequenced using primers labeled at their 5' end with T4 polynucleotide kinase, employing SequiTherm Polymerase. (Epicentre Technologies). The intron-exon borders of selected exons is also determined and genomic PCR products analyzed to confirm the results. PCR products harboring suspected mutations is then cloned and sequenced to validate the results of the direct sequencing.

PCR products is cloned into T-tailed vectors as described in Holton, T. A. and Graham, M. W., Nucleic Acids Research, 19:1156 (1991) and sequenced with T7 polymerase (United States Biochemical). Affected individuals are identified by mutations not present in unaffected individuals.

Genomic rearrangements are also observed as a method of determining alterations in a gene corresponding to a polynucleotide. Genomic clones isolated according to Example 2 are nick-translated with digoxigenindeoxy-uridine 5'-triphosphate (Boehringer Manheim), and FISH performed as described in Johnson, Cg. et al., Methods Cell Biol. 35:73–99 (1991). Hybridization with the labeled probe is carried out using a vast excess of human cot-1 DNA for specific hybridization to the corresponding genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, Cv. et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region hybridized by the probe are identified as insertions, deletions, and translocations. These alterations are used as a diagnostic marker for an associated disease.

Example 12

Method of Detecting Abnormal Levels of a Polypeptide in a Biological Sample

A polypeptide of the present invention can be detected in a biological sample, and if an increased or decreased level of the polypeptide is detected, this polypeptide is a marker for a particular phenotype. Methods of detection are numerous, and thus, it is understood that one skilled in the art can modify the following assay to fit their particular needs.

For example, antibody-sandwich ELISAs are used to detect polypeptides in a sample, preferably a biological sample. Wells of a microtiter plate are coated with specific antibodies, at a final concentration of 0.2 to 10 ug/ml. The antibodies are either monoclonal or polyclonal and are produced by the method described in Example 10. The wells are blocked so that non-specific binding of the polypeptide to the well is reduced.

The coated wells are then incubated for >2 hours at RT with a sample containing the polypeptide. Preferably, serial dilutions of the sample should be used to validate results. The plates are then washed three times with deionized or distilled water to remove unbounded polypeptide.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot polypeptide concentration on the X-axis (log scale) and fluorescence or absorbance of the Y-axis (linear scale). Interpolate the concentration of the polypeptide in the sample using the standard curve.

Example 13

Formulating a Polypeptide

The secreted polypeptide composition will be formulated and dosed in a fashion consistent with good medical practice, taking into account the clinical condition of the individual patient (especially the side effects of treatment with the secreted polypeptide alone), the site of delivery, the method of administration, the scheduling of administration, and other factors known to practitioners. The "effective amount" for purposes herein is thus determined by such considerations.

As a general proposition, the total pharmaceutically effective amount of secreted polypeptide administered parenterally per dose will be in the range of about 1 $\mu$g/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the secreted polypeptide is typically administered at a dose rate of about 1 $\mu$g/kg/hour to about 50 $\mu$g/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the secreted protein of the invention are administered orally, rectally, parenterally, intracistemally, intravaginally, intraperitoneally, opically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The secreted polypeptide is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22:547–556 (1983)), poly (2-hydroxyethyl methacrylate) (R. Langer et al., J. Biomed. Mater. Res. 15:167–277 (1981), and R. Langer, Chem. Tech. 12:98–105 (1982)), ethylene vinyl acetate (R. Langer et al.) or poly-D-(−)-3-hydroxybutyric acid (EP 133,988). Sustained-release compositions also include liposomally entrapped polypeptides. Liposomes containing the secreted polypeptide are prepared by methods known per se: DE 3,218,121; Epstein et al., Proc. Natl. Acad. Sci. USA 82:3688–3692 (1985); Hwang et al., Proc. Natl. Acad. Sci. USA 77:4030–4034 (1980); EP 52,322; EP 36,676; EP 88,046; EP 143,949; EP 142,641; Japanese Pat. Appl. 83–118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal secreted polypeptide therapy.

For parenteral administration, in one embodiment, the secreted polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The secreted polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

Any polypeptide to be used for therapeutic administration can be sterile. Sterility is readily accomplished by filtration through sterile filtration membranes (e.g., 0.2 micron membranes). Therapeutic polypeptide compositions generally are placed into a container having a sterile access port, for example, an intravenous solution bag or vial having a stopper pierceable by a hypodermic injection needle.

Polypeptides ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous polypeptide solution, and the resulting mixture is lyophilized. The infusion solution is prepared by reconstituting the lyophilized polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Example 14

Method of Treating Decreased Levels of the Polypeptide

It will be appreciated that conditions caused by a decrease in the standard or normal expression level of a secreted protein in an individual can be treated by administering the polypeptide of the present invention, preferably in the secreted form. Thus, the invention also provides a method of treatment of an individual in need of an increased level of the polypeptide comprising administering to such an individual a pharmaceutical composition comprising an amount of the polypeptide to increase the activity level of the polypeptide in such an individual.

For example, a patient with decreased levels of a polypeptide receives a daily dose 0.1–100 ug/kg of the polypeptide for six consecutive days. Preferably, the polypeptide is in the secreted form. The exact details of the dosing scheme, based on administration and formulation, are provided in Example 23.

Example 15

Method of Treating Increased Levels of the Polypeptide

Antisense technology is used to inhibit production of a polypeptide of the present invention. This technology is one example of a method of decreasing levels of a polypeptide, preferably a secreted form, due to a variety of etiologies, such as cancer.

For example, a patient diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided in Example 23.

Example 16

Method of Treatment Using Gene Therapy

One method of gene therapy transplants fibroblasts, which are capable of expressing a polypeptide, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37° C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in Example 1. Preferably, the 5' primer contains an EcoRi site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector has the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties.

What is claimed is:

1. An isolated protein comprising an amino acid sequence selected from the group consisting of:

(a) amino acid residues 1 to 316 of SEQ ID NO:10;

(b) amino acid residues 2 to 316 of SEQ ID NO:10; and (c) amino acid residues 50 to 316 of SEQ ID NO:10.

2. The isolated protein of claim 1 which comprises amino acid sequence (a).

3. The isolated protein of claim 1 which comprises amino acid sequence (b).

4. The isolated protein of claim 1 which comprises amino acid sequence (c).

5. The isolated protein of claim 1 wherein the amino acid sequence further comprises a heterologous polypeptide.

6. The isolated protein of claim 5 wherein the heterologous polypeptide is the Fc domain of immunoglobulin.

7. The isolated protein of claim 1 wherein said isolated protein is glycosylated.

8. The isolated protein of claim 1 wherein said isolated protein is fused to polyethylene glycol.

9. A protein produced by a method comprising expressing:

(a) a nucleic acid encoding the protein of claim 1 in a host cell transformed with said nucleic acid; and, (b) recovering said protein.

10. A composition comprising the isolated protein of claim 1 and a pharmaceutically acceptable carrier.

11. An isolated protein comprising an amino acid sequence selected from the group consisting of:

(a) an amino acid sequence of the full-length polypeptide encoded by the HKAEF09 cDNA contained in ATCC Deposit No. 209644;

(b) an amino acid sequence of the full-length polypeptide, excluding the N-terminal methionine residue, encoded by the HKAEF09 cDNA contained in ATCC Deposit No. 209644; and (c) an amino acid sequence of the secreted portion of the polypeptide encoded by the HKAEF09 cDNA contained in ATCC Deposit No. 209644.

12. The isolated protein of claim 11 which comprises amino acid sequence (a).

13. The isolated protein of claim 11 which comprises amino acid sequence (b).

14. The isolated protein of claim 11 which comprises amino acid sequence (c).

15. The isolated protein of claim 11 wherein the amino acid sequence further comprises a heterologous polypeptide.

16. The isolated protein of claim 15 wherein the heterologous polypeptide is the Fc domain of immunoglobulin.

17. The isolated protein of claim 11 wherein said isolated protein is glycosylated.

18. The isolated protein of claim 11 wherein said isolated protein is fused to polyethylene glycol.

19. A protein produced by a method comprising expressing:

(a) a nucleic acid encoding the protein of claim 11 in a host cell transformed with said nucleic acid; and, (b) recovering said protein.

20. A composition comprising the isolated protein of claim 11 and a pharmaceutically acceptable carrier.

21. An isolated protein consisting of an amino acid sequence selected from the group consisting of:

(a) at least 30 contiguous amino acid residues of SEQ ID NO:10;

(b) at least 50 contiguous amino acid residues of SEQ ID NO:10;

(c) at least 30 contiguous amino acid residues of amino acid residues 50 to 316 of SEQ ID NO:10; and (d) at least 50 contiguous amino acid residues of amino acid residues 50 to 316 of SEQ ID NO:10.

22. The isolated protein of claim 21 which comprises amino acid sequence (a).

23. The isolated protein of claim 21 which comprises amino acid sequence (b).

24. The isolated protein of claim 21 which comprises amino acid sequence (c).

25. The isolated protein of claim 21 which comprises amino acid sequence (d).

26. The isolated protein of claim 21 wherein the amino acid sequence further comprises a heterologous polypeptide.

27. The isolated protein of claim 26 wherein the heterologous polypeptide is the Fc domain of immunoglobulin.

28. The isolated protein of claim 21 wherein said isolated protein is glycosylated.

29. The isolated protein of claim 21 wherein said isolated protein is fused to polyethylene glycol.

30. A protein produced by a method comprising expressing:

(a) a nucleic acid encoding the protein of claim 21 in a host cell transformed with said nucleic acid; and, (b) recovering said protein.

31. A composition comprising the isolated protein of claim 21 and a pharmaceutically acceptable carrier.

32. An isolated protein consisting of an amino acid sequence selected from the group consisting of:

(a) at least 30 contiguous amino acid residues encoded by the HKAEF09 cDNA contained in ATCC Deposit No. 209644;

(b) at least 30 contiguous amino acid residues of the secreted portion of the polypeptide encoded by the HKAEF09 cDNA contained in ATCC Deposit No. 209644;

(c) at least 50 contiguous amino acid residues encoded by the HKAEF09 cDNA contained in ATCC Deposit No. 209644; and (d) at least 50 contiguous amino acid residues of the secreted portion of the polypeptide encoded by the HKAEF09 cDNA contained in ATCC Deposit No. 209644.

33. The isolated protein of claim 32 which comprises amino acid sequence (a).

34. The isolated protein of claim 32 which comprises amino acid sequence (b).

35. The isolated protein of claim 32 which comprises amino acid sequence (c).

36. The isolated protein of claim 32 which comprises amino acid sequence (d).

37. The isolated protein of claim 32 wherein the amino acid sequence further comprises a heterologous polypeptide.

38. The isolated protein of claim 37 wherein the heterologous polypeptide is the Fc domain of immunoglobulin.

39. The isolated protein of claim 32 wherein said isolated protein is glycosylated.

40. The isolated protein of claim 32 wherein said isolated protein is fused to polyethylene glycol.

41. A protein produced by a method comprising expressing:

(a) a nucleic acid encoding the protein of claim 32 in a host cell transformed with said nucleic acid; and, (b) recovering said protein.

42. A composition comprising the isolated protein of claim 32 and a pharmaceutically acceptable carrier.

* * * * *

UNITED STATES PATENT AND TRADEMARK OFFICE
CERTIFICATE OF CORRECTION

PATENT NO. : 6,566,498 B1
DATED : May 20, 2003
INVENTOR(S) : Ni et al.

It is certified that error appears in the above-identified patent and that said Letters Patent is hereby corrected as shown below:

Column 1,
Line 2, please delete "now abandoned" and replace with -- copending --.

Column 77,
Lines 34-35, please delete "expressing".
Line 36, please insert -- expressing -- after "(a)".

Column 78,
Lines 13-14, please delete "expressing".
Line 15, please insert -- expressing -- after "(a)".
Lines 48-49, please delete "expressing".
Line 50, please insert -- expressing -- after "(a)".

Column 80,
Lines 5-6, please delete "expressing".
Line 7, please insert -- expressing -- after "(a)".

Signed and Sealed this

Eleventh Day of May, 2004

JON W. DUDAS
*Acting Director of the United States Patent and Trademark Office*

SEQUENCE LISTING

<160> NUMBER OF SEQ ID NOS: 13

<210> SEQ ID NO 1
<211> LENGTH: 1062
<212> TYPE: DNA
<213> ORGANISM: Homo sapiens
<220> FEATURE:
<221> NAME/KEY: CDS
<222> LOCATION: (25)..(876)

<400> SEQUENCE: 1

```
cacgagcgcc agcctgcgtc tgcc atg ggg ctc ggg ttg agg ggc tgg gga          51
                         Met Gly Leu Gly Leu Arg Gly Trp Gly
                           1               5 cgt cct ctg ctg act gtg gcc acc gcc ctg atg ctg ccc gtg aag ccc          99
Arg Pro Leu Leu Thr Val Ala Thr Ala Leu Met Leu Pro Val Lys Pro
 10              15                  20                  25 ccc gca ggc tcc tgg ggg gcc cag atc atc ggg ggc cac gag gtg acc         147
Pro Ala Gly Ser Trp Gly Ala Gln Ile Ile Gly Gly His Glu Val Thr
                 30                  35                  40 ccc cac tcc agg ccc tac atg gca tcc gtg cgc ttc ggg ggc caa cat         195
Pro His Ser Arg Pro Tyr Met Ala Ser Val Arg Phe Gly Gly Gln His
             45                  50                  55 cac tgc gga ggc ttc ctg ctg cga gcc cgc tgg gtg gtc tcg gcc gcc         243
His Cys Gly Gly Phe Leu Leu Arg Ala Arg Trp Val Val Ser Ala Ala
         60                  65                  70 cac tgc ttc agc cac aga gac ctc cgc act ggc ctg gtg gtg ctg ggc         291
His Cys Phe Ser His Arg Asp Leu Arg Thr Gly Leu Val Val Leu Gly
     75                  80                  85 gcc cac gtc ctg agt act gcg gag ccc acc cag cag gtg ttt ggc atc         339
Ala His Val Leu Ser Thr Ala Glu Pro Thr Gln Gln Val Phe Gly Ile
 90                  95                 100                 105 gat gct ctc acc acg cac ccc gac tac cac ccc atg acc cac gcc aac         387
Asp Ala Leu Thr Thr His Pro Asp Tyr His Pro Met Thr His Ala Asn
                110                 115                 120 gac atc tgc ctg ctg cgg ctg aac ggc tct gct gtc ctg ggc cct gca         435
Asp Ile Cys Leu Leu Arg Leu Asn Gly Ser Ala Val Leu Gly Pro Ala
            125                 130                 135 gtg ggg ctg ctg agg ctg cca ggg aga agg gcc agg ccc cca aca gcg         483
Val Gly Leu Leu Arg Leu Pro Gly Arg Arg Ala Arg Pro Pro Thr Ala
        140                 145                 150 ggg aca cgg tgc cgg gtg gct ggc tgg ggc ttc gtg tct gac ttt gag         531
Gly Thr Arg Cys Arg Val Ala Gly Trp Gly Phe Val Ser Asp Phe Glu
    155                 160                 165 gag ctg ccg cct gga ctg atg gag gcc aag gtc cga gtg ctg gac ccg         579
Glu Leu Pro Pro Gly Leu Met Glu Ala Lys Val Arg Val Leu Asp Pro
170                 175                 180                 185 gac gtc tgc aac agc tcc tgg aag ggc cac ctg aca ctt acc atg ctc         627
Asp Val Cys Asn Ser Ser Trp Lys Gly His Leu Thr Leu Thr Met Leu
                190                 195                 200 tgc acc cgc agt ggg gac agc cac aga cgg ggc ttc tgc tcg gcc gac         675
Cys Thr Arg Ser Gly Asp Ser His Arg Arg Gly Phe Cys Ser Ala Asp
            205                 210                 215 tcc gga ggg ccc ctg gtg tgc agg aac cgg gct cac ggc ctc gtt tcc         723
Ser Gly Gly Pro Leu Val Cys Arg Asn Arg Ala His Gly Leu Val Ser
```

```
                220                    225                      230
ttc tcg ggc ctc tgg tgc ggc gac ccc aag acc ccc gac gtg tac acg     771
Phe Ser Gly Leu Trp Cys Gly Asp Pro Lys Thr Pro Asp Val Tyr Thr
    235                    240                      245 cag gtg tcc gcc ttt gtg gcc tgg atc tgg gac gtg gtt cgg cgg agc     819
Gln Val Ser Ala Phe Val Ala Trp Ile Trp Asp Val Val Arg Arg Ser
250                    255                      260                265 agt ccc cag ccc ggc ccc ctg cct ggg acc acc agg ccc cca gga gaa     867
Ser Pro Gln Pro Gly Pro Leu Pro Gly Thr Thr Arg Pro Pro Gly Glu
                   270                    275                      280 gcc gcc tga gccacaacct tgcggcatgc aaatgagatg ccgctccag              916
Ala Ala gcctggaatg ttccgtggct gggccccacg ggaagcctga tgttcagggt tggggtggga   976
cgggcagcgg tggggcacac ccattccaca tgcaagggc agaagcaaac ccagtaaaat   1036
gttaactgac aaaaaaaaaa aaaaaa                                       1062

<210> SEQ ID NO 2
<211> LENGTH: 283
<212> TYPE: PRT
<213> ORGANISM: Homo sapiens

<400> SEQUENCE: 2

Met Gly Leu Gly Leu Arg Gly Trp Gly Arg Pro Leu Leu Thr Val Ala
1               5                   10                  15

Thr Ala Leu Met Leu Pro Val Lys Pro Pro Ala Gly Ser Trp Gly Ala
            20                  25                  30

Gln Ile Ile Gly Gly His Glu Val Thr Pro His Ser Arg Pro Tyr Met
        35                  40                  45

Ala Ser Val Arg Phe Gly Gly Gln His His Cys Gly Gly Phe Leu Leu
    50                  55                  60

Arg Ala Arg Trp Val Val Ser Ala Ala His Cys Phe Ser His Arg Asp
65                  70                  75                  80

Leu Arg Thr Gly Leu Val Val Leu Gly Ala His Val Leu Ser Thr Ala
                85                  90                  95

Glu Pro Thr Gln Gln Val Phe Gly Ile Asp Ala Leu Thr Thr His Pro
            100                 105                 110

Asp Tyr His Pro Met Thr His Ala Asn Asp Ile Cys Leu Leu Arg Leu
        115                 120                 125

Asn Gly Ser Ala Val Leu Gly Pro Ala Val Gly Leu Leu Arg Leu Pro
    130                 135                 140

Gly Arg Arg Ala Arg Pro Pro Thr Ala Gly Thr Arg Cys Arg Val Ala
145                 150                 155                 160

Gly Trp Gly Phe Val Ser Asp Phe Glu Glu Leu Pro Pro Gly Leu Met
                165                 170                 175

Glu Ala Lys Val Arg Val Leu Asp Pro Asp Val Cys Asn Ser Ser Trp
            180                 185                 190

Lys Gly His Leu Thr Leu Thr Met Leu Cys Thr Arg Ser Gly Asp Ser
        195                 200                 205

His Arg Arg Gly Phe Cys Ser Ala Asp Ser Gly Gly Pro Leu Val Cys
    210                 215                 220

Arg Asn Arg Ala His Gly Leu Val Ser Phe Ser Gly Leu Trp Cys Gly
225                 230                 235                 240

Asp Pro Lys Thr Pro Asp Val Tyr Thr Gln Val Ser Ala Phe Val Ala
                245                 250                 255
```

```
Trp Ile Trp Asp Val Val Arg Arg Ser Ser Pro Gln Pro Gly Pro Leu
        260                 265                 270

Pro Gly Thr Thr Arg Pro Pro Gly Glu Ala Ala
        275                 280

<210> SEQ ID NO 3
<211> LENGTH: 792
<212> TYPE: DNA
<213> ORGANISM: Homo sapiens
<220> FEATURE:
<221> NAME/KEY: CDS
<222> LOCATION: (85)..(708)

<400> SEQUENCE: 3
gacccacgcg tccggtactg gggcctcctc cactgggtcc gaatcagtag gtgaccccgc      60
ccctggattc tggaagacct cacc atg gga cgc ccc cga cct cgt gcg gcc       111
                          Met Gly Arg Pro Arg Pro Arg Ala Ala
                            1               5 aag acg tgg atg ttc ctg ctc ttg ctg ggg gga gcc tgg gca ggg aaa      159
Lys Thr Trp Met Phe Leu Leu Leu Leu Gly Gly Ala Trp Ala Gly Lys
 10              15                  20                  25 tac aca gta cgc ctg gga gac cac agc cta cag aat aaa gat ggc cca      207
Tyr Thr Val Arg Leu Gly Asp His Ser Leu Gln Asn Lys Asp Gly Pro
         30                  35                  40 gag caa gaa ata cct gtg gtt cag tcc atc cca cac ccc tgc tac aac      255
Glu Gln Glu Ile Pro Val Val Gln Ser Ile Pro His Pro Cys Tyr Asn
             45                  50                  55 agc agc gat gtg gag gac cac aac cat gat ctg atg ctt ctt caa ctg      303
Ser Ser Asp Val Glu Asp His Asn His Asp Leu Met Leu Leu Gln Leu
 60                  65                  70 cgt gac cag gca tcc ctg ggg tcc aaa gtg aag ccc atc agc ctg gca      351
Arg Asp Gln Ala Ser Leu Gly Ser Lys Val Lys Pro Ile Ser Leu Ala
         75                  80                  85 gat cat tgc acc cag ctg gcc aga agt gca ccg tct cag gct ggg ggc      399
Asp His Cys Thr Gln Leu Ala Arg Ser Ala Pro Ser Gln Ala Gly Gly
     90                  95                 100                 105 act gtc acc agt ccc cga gag aat ttt cct gac act ctc aac tgt gca      447
Thr Val Thr Ser Pro Arg Glu Asn Phe Pro Asp Thr Leu Asn Cys Ala
                110                 115                 120 gaa gta aaa tct ttc ccc cag aag aag tgt gag gat gct tac ccg ggg      495
Glu Val Lys Ser Phe Pro Gln Lys Lys Cys Glu Asp Ala Tyr Pro Gly
         125                 130                 135 cag atc aca gat ggc atg gtc tgt gca ggc agc agc aaa ggg gct gac      543
Gln Ile Thr Asp Gly Met Val Cys Ala Gly Ser Ser Lys Gly Ala Asp
     140                 145                 150 acg tgc cag ggc gat tct gga ggc ccc ctg gtg tgt gat ggt gca ctc      591
Thr Cys Gln Gly Asp Ser Gly Gly Pro Leu Val Cys Asp Gly Ala Leu
155                 160                 165 cag ggc atc aca tcc tgg ggc tca gac ccc tgt ggg agg tcc gac aaa      639
Gln Gly Ile Thr Ser Trp Gly Ser Asp Pro Cys Gly Arg Ser Asp Lys
170                 175                 180                 185 cct ggc gtc tat acc aac atc tgc cgc tac ctg gac tgg atc aag aag      687
Pro Gly Val Tyr Thr Asn Ile Cys Arg Tyr Leu Asp Trp Ile Lys Lys
                190                 195                 200 atc ata ggc agc aag ggc tga ttttaggata agcaccgatc tcccttaata         738
Ile Ile Gly Ser Lys Gly
                205 aactcacaac tctctggttc aaaaaaaaaa aaaaaaaaaa aaaaaaaaaa aaaa           790

<210> SEQ ID NO 4
```

```
<211> LENGTH: 207
<212> TYPE: PRT
<213> ORGANISM: Homo sapiens

<400> SEQUENCE: 4

Met Gly Arg Pro Arg Pro Arg Ala Ala Lys Thr Trp Met Phe Leu Leu
 1               5                  10                  15

Leu Leu Gly Gly Ala Trp Ala Gly Lys Tyr Thr Val Arg Leu Gly Asp
            20                  25                  30

His Ser Leu Gln Asn Lys Asp Gly Pro Glu Gln Glu Ile Pro Val Val
        35                  40                  45

Gln Ser Ile Pro His Pro Cys Tyr Asn Ser Ser Asp Val Glu Asp His
    50                  55                  60

Asn His Asp Leu Met Leu Gln Leu Arg Asp Gln Ala Ser Leu Gly
65                  70                  75                  80

Ser Lys Val Lys Pro Ile Ser Leu Ala Asp His Cys Thr Gln Leu Ala
                85                  90                  95

Arg Ser Ala Pro Ser Gln Ala Gly Gly Thr Val Thr Ser Pro Arg Glu
            100                 105                 110

Asn Phe Pro Asp Thr Leu Asn Cys Ala Glu Val Lys Ser Phe Pro Gln
        115                 120                 125

Lys Lys Cys Glu Asp Ala Tyr Pro Gly Gln Ile Thr Asp Gly Met Val
    130                 135                 140

Cys Ala Gly Ser Ser Lys Gly Ala Asp Thr Cys Gln Gly Asp Ser Gly
145                 150                 155                 160

Gly Pro Leu Val Cys Asp Gly Ala Leu Gln Gly Ile Thr Ser Trp Gly
                165                 170                 175

Ser Asp Pro Cys Gly Arg Ser Asp Lys Pro Gly Val Tyr Thr Asn Ile
            180                 185                 190

Cys Arg Tyr Leu Asp Trp Ile Lys Ile Ile Gly Ser Lys Gly
        195                 200                 205

<210> SEQ ID NO 5
<211> LENGTH: 840
<212> TYPE: DNA
<213> ORGANISM: Homo sapiens
<220> FEATURE:
<221> NAME/KEY: CDS
<222> LOCATION: (115)..(603)

<400> SEQUENCE: 5
cgggtcgacc cacgcgtccg ggacgagaga tagcagcgac gcgacaggcc aaacagtgac        60
agccacgtag aggatctggc agacaaagag acaagacttt ggaagtgacc cacc atg       117
                                                             Met
                                                               1 ggg ctc agc atc ttt ttg ctc ctg tgt gtt ctt ggg ctc agc cag gca       165
Gly Leu Ser Ile Phe Leu Leu Leu Cys Val Leu Gly Leu Ser Gln Ala
              5                  10                  15 gcc aca ccg aag att ttc aat ggc act gag tgt ggg cgt aac tca cag       213
Ala Thr Pro Lys Ile Phe Asn Gly Thr Glu Cys Gly Arg Asn Ser Gln
            20                  25                  30 ccg tgg cag gtg ggg ctg ttt gag ggc acc agc ctg cgc tgc ggg ggt       261
Pro Trp Gln Val Gly Leu Phe Glu Gly Thr Ser Leu Arg Cys Gly Gly
        35                  40                  45 gtc ctt att gac cac agg tgg gtc ctc aca gcg gct cac tgg cag cgg       309
Val Leu Ile Asp His Arg Trp Val Leu Thr Ala Ala His Trp Gln Arg
    50                  55                  60                  65 cag acc cat tcc ccg gat ctg ctc cag tgc ctc aac ctc tcc atc gtc       357
```

```
Gln Thr His Ser Pro Asp Leu Leu Gln Cys Leu Asn Leu Ser Ile Val
                 70                  75                  80 tcc cat gcc acc tgc cat ggt gtg tat ccc ggg aga atc acg agc aac      405
Ser His Ala Thr Cys His Gly Val Tyr Pro Gly Arg Ile Thr Ser Asn
                 85                  90                  95 atg gtg tgt gca ggc ggc gtc ccg ggg caa gat gcc tgc cag ggt gat      453
Met Val Cys Ala Gly Gly Val Pro Gly Gln Asp Ala Cys Gln Gly Asp
            100                 105                 110 tct ggg ggc ccc ctg gtg tgt ggg gga gtc ctt caa ggt ctg gtg tcc      501
Ser Gly Gly Pro Leu Val Cys Gly Gly Val Leu Gln Gly Leu Val Ser
        115                 120                 125 tgg ggg tct gtg ggg ccc tgt gga caa gat ggc atc cct gga gtc tac      549
Trp Gly Ser Val Gly Pro Cys Gly Gln Asp Gly Ile Pro Gly Val Tyr
130                 135                 140                 145 acc tat att tgc aag tat gtg gac tgg atc cgg atg atc atg agg aac      597
Thr Tyr Ile Cys Lys Tyr Val Asp Trp Ile Arg Met Ile Met Arg Asn
                150                 155                 160 aac tga cctgtttcct ccacctccac ccccacccct taacttgggt acccctctgg       653
Asn ccctcagagc accaatatct cctccatcac ttccctagc tccactcttg ttggcctggg     713
aacttcttgg aactttaact cctgccagcc cttctaagac ccacgagcgg ggtgagagaa    773
gtgtgcaata gtctggaata aatataaatg aaggagggaa aaaaaaaaaa aaaaaaaaaa    833
aaaaaaa                                                              840

<210> SEQ ID NO 6
<211> LENGTH: 162
<212> TYPE: PRT
<213> ORGANISM: Homo sapiens

<400> SEQUENCE: 6

Met Gly Leu Ser Ile Phe Leu Leu Cys Val Leu Gly Leu Ser Gln
  1               5                  10                  15

Ala Ala Thr Pro Lys Ile Phe Asn Gly Thr Glu Cys Gly Arg Asn Ser
                 20                  25                  30

Gln Pro Trp Gln Val Gly Leu Phe Glu Gly Thr Ser Leu Arg Cys Gly
             35                  40                  45

Gly Val Leu Ile Asp His Arg Trp Val Leu Thr Ala Ala His Trp Gln
         50                  55                  60

Arg Gln Thr His Ser Pro Asp Leu Leu Gln Cys Leu Asn Leu Ser Ile
 65                  70                  75                  80

Val Ser His Ala Thr Cys His Gly Val Tyr Pro Gly Arg Ile Thr Ser
                 85                  90                  95

Asn Met Val Cys Ala Gly Gly Val Pro Gly Gln Asp Ala Cys Gln Gly
            100                 105                 110

Asp Ser Gly Gly Pro Leu Val Cys Gly Gly Val Leu Gln Gly Leu Val
        115                 120                 125

Ser Trp Gly Ser Val Gly Pro Cys Gly Gln Asp Gly Ile Pro Gly Val
130                 135                 140

Tyr Thr Tyr Ile Cys Lys Tyr Val Asp Trp Ile Arg Met Ile Met Arg
145                 150                 155                 160

Asn Asn

<210> SEQ ID NO 7
<211> LENGTH: 1527
<212> TYPE: DNA
<213> ORGANISM: Homo sapiens
```

```
<220> FEATURE:
<221> NAME/KEY: CDS
<222> LOCATION: (67)..(1335)

<400> SEQUENCE: 7
tacgaggtgg gtagaggtga tgcagtgctg aagacctggg cccctgctca gtgcctttgc     60 tctaga atg ggt cca gct tgg ctt tgg cta ctg gga aca ggg atc ctg        108
       Met Gly Pro Ala Trp Leu Trp Leu Leu Gly Thr Gly Ile Leu
         1               5                  10 gcc tct gtc cac tgt cag ccc ctt ctt gcc cat gga gat aaa agt ctg       156
Ala Ser Val His Cys Gln Pro Leu Leu Ala His Gly Asp Lys Ser Leu
 15              20                  25                  30 cag ggg cct caa ccc ccc agg cat cag ctc tca gag cca gcc ccc gcc       204
Gln Gly Pro Gln Pro Pro Arg His Gln Leu Ser Glu Pro Ala Pro Ala
             35                  40                  45 tac cac aga atc aca ccc acc att acc aat ttt gct ttg cgt ttg tat       252
Tyr His Arg Ile Thr Pro Thr Ile Thr Asn Phe Ala Leu Arg Leu Tyr
 50                  55                  60 aaa gag ctg gca gca gac gcc ccc gga aac atc ttc ttc tcg cca gtg       300
Lys Glu Leu Ala Ala Asp Ala Pro Gly Asn Ile Phe Phe Ser Pro Val
 65                  70                  75 agc atc tcc acc acc ctg gcc ctg ctc tct ctt ggg gcc caa gct aac       348
Ser Ile Ser Thr Thr Leu Ala Leu Leu Ser Leu Gly Ala Gln Ala Asn
 80                  85                  90 acc tca gct ctg atc ctg gag ggc ctg gga ttc aac ctc aca gaa acc       396
Thr Ser Ala Leu Ile Leu Glu Gly Leu Gly Phe Asn Leu Thr Glu Thr
 95                 100                 105                 110 cct gaa gcc gac atc cac cag ggc ttc cgg agc ctc ctc cac acc ctt       444
Pro Glu Ala Asp Ile His Gln Gly Phe Arg Ser Leu Leu His Thr Leu
                115                 120                 125 gcc ctg ccc agc ccc aaa ctc gaa cta aaa gta gga aac tcc ctg ttc       492
Ala Leu Pro Ser Pro Lys Leu Glu Leu Lys Val Gly Asn Ser Leu Phe
            130                 135                 140 cta gac aag cga cta aag cct cgg cag cac tat ttg gac agc atc aag       540
Leu Asp Lys Arg Leu Lys Pro Arg Gln His Tyr Leu Asp Ser Ile Lys
145                 150                 155 gag ctt tat gga gct ttt gct ttt tct gcc aac ttc aca gat tct gtt       588
Glu Leu Tyr Gly Ala Phe Ala Phe Ser Ala Asn Phe Thr Asp Ser Val
    160                 165                 170 aca act ggg agg cag att aat gac tat ttg aga agg caa aca tac ggg       636
Thr Thr Gly Arg Gln Ile Asn Asp Tyr Leu Arg Arg Gln Thr Tyr Gly
175                 180                 185                 190 caa gtc gtg gac tgc ctc ccg gag ttc agc cag gac acg ttc atg gtt       684
Gln Val Val Asp Cys Leu Pro Glu Phe Ser Gln Asp Thr Phe Met Val
                195                 200                 205 ctt gcc aat tac atc ttc ttc aaa gcc aag tgg aag cac cct ttc agt       732
Leu Ala Asn Tyr Ile Phe Phe Lys Ala Lys Trp Lys His Pro Phe Ser
            210                 215                 220 cgc tac cag acc cag aag cag gaa agt ttc ttt gtg gat gag agg act       780
Arg Tyr Gln Thr Gln Lys Gln Glu Ser Phe Phe Val Asp Glu Arg Thr
        225                 230                 235 tct ctc cag gtc ccc atg atg cac caa aag gaa atg cac aga ttc ctc       828
Ser Leu Gln Val Pro Met Met His Gln Lys Glu Met His Arg Phe Leu
    240                 245                 250 tat gac cag gat ttg gct tgc acc gtc ctc cag ata gaa tac aga gga       876
Tyr Asp Gln Asp Leu Ala Cys Thr Val Leu Gln Ile Glu Tyr Arg Gly
255                 260                 265                 270 aat gcc ttg gcg ctg ctg gtc ctc cct gac ccg ggg aaa atg aag cag       924
Asn Ala Leu Ala Leu Leu Val Leu Pro Asp Pro Gly Lys Met Lys Gln
                275                 280                 285
```

-continued

| | |
|---|---|
| gtg gag gct gct ctg cag cca cag acc ctg aga aaa tgg ggc caa ttg<br>Val Glu Ala Ala Leu Gln Pro Gln Thr Leu Arg Lys Trp Gly Gln Leu<br>              290                            295                          300 | 972 |
| ctc ctg ccc agt ctg ttg gat ttg cac ttg cca agg ttt tca att tct<br>Leu Leu Pro Ser Leu Leu Asp Leu His Leu Pro Arg Phe Ser Ile Ser<br>                    305                            310                          315 | 1020 |
| gga aca tat aac ctg gaa gac ata ctt ccc caa att ggt ctc acc aac<br>Gly Thr Tyr Asn Leu Glu Asp Ile Leu Pro Gln Ile Gly Leu Thr Asn<br>320                            325                          330 | 1068 |
| ata ctc aac tta gaa gct gac ttc tca gga gtc act ggg cag ctc aac<br>Ile Leu Asn Leu Glu Ala Asp Phe Ser Gly Val Thr Gly Gln Leu Asn<br>335                        340                          345                      350 | 1116 |
| aaa acc atc tcc aag gtg tca cac aag gcg atg gtg gac atg agt gag<br>Lys Thr Ile Ser Lys Val Ser His Lys Ala Met Val Asp Met Ser Glu<br>                    355                            360                          365 | 1164 |
| aag ggg acc gag gcc ggg gct gct tca ggc ctc ctc tcc cag ccc cca<br>Lys Gly Thr Glu Ala Gly Ala Ala Ser Gly Leu Leu Ser Gln Pro Pro<br>                    370                            375                          380 | 1212 |
| tct ctg aac acc atg tca gac cca cat gcc cac ttc aac agg cct ttc<br>Ser Leu Asn Thr Met Ser Asp Pro His Ala His Phe Asn Arg Pro Phe<br>385                            390                          395 | 1260 |
| ctc ttg ctc ctt tgg gag gtc acc acc cag agc tta ctc ttc ctg gga<br>Leu Leu Leu Leu Trp Glu Val Thr Thr Gln Ser Leu Leu Phe Leu Gly<br>                    400                            405                          410 | 1308 |
| aaa gtt gtc aac cca gtt gca ggg taa ccatggtggg aggccaggag<br>Lys Val Val Asn Pro Val Ala Gly<br>415                          420 | 1355 |
| ttatcttatc tcatcctgga ccaaacagat aggccagaac cagcctgcat cctggggctg | 1415 |
| ctatgtggtt cagttaatca gtgtgccaag attctaataa agttgacctt gggttctgtg | 1475 |
| aaaaaaaaaa aaaaaaaaaa aaaaaaaaaa aaaaaaaaaa aaaaaaaaaa aa | 1527 |

<210> SEQ ID NO 8
<211> LENGTH: 422
<212> TYPE: PRT
<213> ORGANISM: Homo sapiens

<400> SEQUENCE: 8

Met Gly Pro Ala Trp Leu Trp Leu Leu Gly Thr Gly Ile Leu Ala Ser
1               5                   10                  15

Val His Cys Gln Pro Leu Leu Ala His Gly Asp Lys Ser Leu Gln Gly
                20                  25                  30

Pro Gln Pro Pro Arg His Gln Leu Ser Glu Pro Ala Pro Ala Tyr His
            35                  40                  45

Arg Ile Thr Pro Thr Ile Thr Asn Phe Ala Leu Arg Leu Tyr Lys Glu
        50                  55                  60

Leu Ala Ala Asp Ala Pro Gly Asn Ile Phe Phe Ser Pro Val Ser Ile
65                  70                  75                  80

Ser Thr Thr Leu Ala Leu Leu Ser Leu Gly Ala Gln Ala Asn Thr Ser
                85                  90                  95

Ala Leu Ile Leu Glu Gly Leu Gly Phe Asn Leu Thr Glu Thr Pro Glu
            100                 105                 110

Ala Asp Ile His Gln Gly Phe Arg Ser Leu Leu His Thr Leu Ala Leu
        115                 120                 125

Pro Ser Pro Lys Leu Glu Leu Lys Val Gly Asn Ser Leu Phe Leu Asp
    130                 135                 140

Lys Arg Leu Lys Pro Arg Gln His Tyr Leu Asp Ser Ile Lys Glu Leu

```
145                 150                 155                 160
Tyr Gly Ala Phe Ala Phe Ser Ala Asn Phe Thr Asp Ser Val Thr Thr
                165                 170                 175

Gly Arg Gln Ile Asn Asp Tyr Leu Arg Arg Gln Thr Tyr Gly Gln Val
            180                 185                 190

Val Asp Cys Leu Pro Glu Phe Ser Gln Asp Thr Phe Met Val Leu Ala
        195                 200                 205

Asn Tyr Ile Phe Phe Lys Ala Lys Trp Lys His Pro Phe Ser Arg Tyr
    210                 215                 220

Gln Thr Gln Lys Gln Glu Ser Phe Phe Val Asp Glu Arg Thr Ser Leu
225                 230                 235                 240

Gln Val Pro Met Met His Gln Lys Glu Met His Arg Phe Leu Tyr Asp
                245                 250                 255

Gln Asp Leu Ala Cys Thr Val Leu Gln Ile Glu Tyr Arg Gly Asn Ala
            260                 265                 270

Leu Ala Leu Leu Val Leu Pro Asp Pro Gly Lys Met Lys Gln Val Glu
        275                 280                 285

Ala Ala Leu Gln Pro Gln Thr Leu Arg Lys Trp Gly Gln Leu Leu Leu
    290                 295                 300

Pro Ser Leu Leu Asp Leu His Leu Pro Arg Phe Ser Ile Ser Gly Thr
305                 310                 315                 320

Tyr Asn Leu Glu Asp Ile Leu Pro Gln Ile Gly Leu Thr Asn Ile Leu
                325                 330                 335

Asn Leu Glu Ala Asp Phe Ser Gly Val Thr Gly Gln Leu Asn Lys Thr
            340                 345                 350

Ile Ser Lys Val Ser His Lys Ala Met Val Asp Met Ser Glu Lys Gly
        355                 360                 365

Thr Glu Ala Gly Ala Ala Ser Gly Leu Leu Ser Gln Pro Pro Ser Leu
    370                 375                 380

Asn Thr Met Ser Asp Pro His Ala His Phe Asn Arg Pro Phe Leu Leu
385                 390                 395                 400

Leu Leu Trp Glu Val Thr Thr Gln Ser Leu Leu Phe Leu Gly Lys Val
                405                 410                 415

Val Asn Pro Val Ala Gly
            420

<210> SEQ ID NO 9
<211> LENGTH: 1405
<212> TYPE: DNA
<213> ORGANISM: Homo sapiens
<220> FEATURE:
<221> NAME/KEY: CDS
<222> LOCATION: (70)..(1017)

<400> SEQUENCE: 9
ggtcgaccca cgcgtccgtg cccagccacc accgtctctc caaaaacccg aggtctcgct      60 aaaatcatc atg gat tca ctt ggc gcc gtc agc act cga ctt ggg ttt gat    111
          Met Asp Ser Leu Gly Ala Val Ser Thr Arg Leu Gly Phe Asp
            1               5                  10 ctt ttc aaa gag ctg aag aaa aca aat gat ggc aac atc ttc ttt tcc      159
Leu Phe Lys Glu Leu Lys Lys Thr Asn Asp Gly Asn Ile Phe Phe Ser
 15                  20                  25                  30 cct gtg ggc atc ttg act gca att ggc atg gtc ctc ctg ggg acc cga      207
Pro Val Gly Ile Leu Thr Ala Ile Gly Met Val Leu Leu Gly Thr Arg
                 35                  40                  45 gga gcc acc gct tcc cag ttg gag gag gtg ttt cac tct gaa aaa gag      255
```

```
Gly Ala Thr Ala Ser Gln Leu Glu Glu Val Phe His Ser Glu Lys Glu
             50                  55                  60 acg aag agc tca aga ata aag gct gaa gaa aaa gag gtg att gag aac    303
Thr Lys Ser Ser Arg Ile Lys Ala Glu Glu Lys Glu Val Ile Glu Asn
         65                  70                  75 aca gaa gca gta cat caa caa ttc caa aag ttt ttg act gaa ata agc    351
Thr Glu Ala Val His Gln Gln Phe Gln Lys Phe Leu Thr Glu Ile Ser
     80                  85                  90 aaa ctc act aat gat tat gaa ctg aac ata acc aac agg ctg ttt gga    399
Lys Leu Thr Asn Asp Tyr Glu Leu Asn Ile Thr Asn Arg Leu Phe Gly
 95                 100                 105                 110 gaa aaa aca tac ctc ttc ctt caa aaa tac tta gat tat gtt gaa aaa    447
Glu Lys Thr Tyr Leu Phe Leu Gln Lys Tyr Leu Asp Tyr Val Glu Lys
                115                 120                 125 tat tat cat gca tct ctg gaa cct gtt gat ttt gta aat gca gcc gat    495
Tyr Tyr His Ala Ser Leu Glu Pro Val Asp Phe Val Asn Ala Ala Asp
            130                 135                 140 gaa agt cga aag aag att aat tcc tgg gtt gaa agc aaa aca aat gaa    543
Glu Ser Arg Lys Lys Ile Asn Ser Trp Val Glu Ser Lys Thr Asn Glu
        145                 150                 155 aaa atc aag gac ttg ttc cca gat ggc tct att agt agc tct acc aag    591
Lys Ile Lys Asp Leu Phe Pro Asp Gly Ser Ile Ser Ser Ser Thr Lys
    160                 165                 170 ctg gtg ctg gtg aac atg gtt tat ttt aaa ggg caa tgg gac agt tac    639
Leu Val Leu Val Asn Met Val Tyr Phe Lys Gly Gln Trp Asp Ser Tyr
175                 180                 185                 190 gat cta gag gcg gtc ctg gct gcc atg ggg atg ggc gat gcc ttc agt    687
Asp Leu Glu Ala Val Leu Ala Ala Met Gly Met Gly Asp Ala Phe Ser
                195                 200                 205 gag cac aaa gcc gac tac tcg gga atg tcg tca ggc tcc ggg ttg tac    735
Glu His Lys Ala Asp Tyr Ser Gly Met Ser Ser Gly Ser Gly Leu Tyr
            210                 215                 220 gcc cag aag ttc ctg cac agt tcc ttt gtg gca gta act gag gaa ggc    783
Ala Gln Lys Phe Leu His Ser Ser Phe Val Ala Val Thr Glu Glu Gly
        225                 230                 235 acc gag gct gca gct gcc act ggc ata ggc ttt act gtc aca tcc gcc    831
Thr Glu Ala Ala Ala Ala Thr Gly Ile Gly Phe Thr Val Thr Ser Ala
    240                 245                 250 cca ggt cat gaa aat gtt cac tgc aat cat ccc ttc ctg ttc ttc atc    879
Pro Gly His Glu Asn Val His Cys Asn His Pro Phe Leu Phe Phe Ile
255                 260                 265                 270 agg aac cat gca tcc cca aaa cca agg agc cct gcc acc cca agg tgc    927
Arg Asn His Ala Ser Pro Lys Pro Arg Ser Pro Ala Thr Pro Arg Cys
                275                 280                 285 ctg agc cct gcc acc cca aag tgc ctg agc cct gcc agc cca agg ttc    975
Leu Ser Pro Ala Thr Pro Lys Cys Leu Ser Pro Ala Ser Pro Arg Phe
            290                 295                 300 cag agc cat gcc acc cca agg tgc ctg agc cct gcc ctt caa             1017
Gln Ser His Ala Thr Pro Arg Cys Leu Ser Pro Ala Leu Gln
        305                 310                 315 tagtcactcc agcaccagcc agcagaaga ccaagcagaa gtaatgtggt ccacagccat    1077
gcccttgagg agccggccac cagatgctga atcccctatc ccattctgtg tatgaggtcc    1137
catttgccct tgcaattggc attctgtctc ccccaaaaaa gaatgtgcta tgaagctttc    1197
tttcctacac actctgagtc tctgaatgaa gctgaaggtc ttagtaccca gagctagttt    1257
tcagctgctc agaattcatc tgaagagaga cttaagatga aagcaaatga ttcagctccc    1317 ttatacccccc attaaattca ctttcaattc caaaaaaaaa aaaaaaaaaa aaaaaaaaaa    1377
```

```
aaaaaaaaaa aaaaaaaaaa aaaaaaaa                                        1405

<210> SEQ ID NO 10
<211> LENGTH: 316
<212> TYPE: PRT
<213> ORGANISM: Homo sapiens

<400> SEQUENCE: 10

Met Asp Ser Leu Gly Ala Val Ser Thr Arg Leu Gly Phe Asp Leu Phe
  1               5                  10                  15

Lys Glu Leu Lys Lys Thr Asn Asp Gly Asn Ile Phe Phe Ser Pro Val
             20                  25                  30

Gly Ile Leu Thr Ala Ile Gly Met Val Leu Leu Gly Thr Arg Gly Ala
         35                  40                  45

Thr Ala Ser Gln Leu Glu Glu Val Phe His Ser Glu Lys Glu Thr Lys
     50                  55                  60

Ser Ser Arg Ile Lys Ala Glu Glu Lys Glu Val Ile Glu Asn Thr Glu
 65                  70                  75                  80

Ala Val His Gln Gln Phe Gln Lys Phe Leu Thr Glu Ile Ser Lys Leu
                 85                  90                  95

Thr Asn Asp Tyr Glu Leu Asn Ile Thr Asn Arg Leu Phe Gly Glu Lys
            100                 105                 110

Thr Tyr Leu Phe Leu Gln Lys Tyr Leu Asp Tyr Val Glu Lys Tyr Tyr
        115                 120                 125

His Ala Ser Leu Glu Pro Val Asp Phe Val Asn Ala Ala Asp Glu Ser
    130                 135                 140

Arg Lys Lys Ile Asn Ser Trp Val Glu Ser Lys Thr Asn Glu Lys Ile
145                 150                 155                 160

Lys Asp Leu Phe Pro Asp Gly Ser Ile Ser Ser Thr Lys Leu Val
                165                 170                 175

Leu Val Asn Met Val Tyr Phe Lys Gly Gln Trp Asp Ser Tyr Asp Leu
                180                 185                 190

Glu Ala Val Leu Ala Ala Met Gly Met Gly Asp Ala Phe Ser Glu His
            195                 200                 205

Lys Ala Asp Tyr Ser Gly Met Ser Ser Gly Ser Gly Leu Tyr Ala Gln
        210                 215                 220

Lys Phe Leu His Ser Ser Phe Val Ala Val Thr Glu Glu Gly Thr Glu
225                 230                 235                 240

Ala Ala Ala Ala Thr Gly Ile Gly Phe Thr Val Thr Ser Ala Pro Gly
                245                 250                 255

His Glu Asn Val His Cys Asn His Pro Phe Leu Phe Phe Ile Arg Asn
                260                 265                 270

His Ala Ser Pro Lys Pro Arg Ser Pro Ala Thr Pro Arg Cys Leu Ser
            275                 280                 285

Pro Ala Thr Pro Lys Cys Leu Ser Pro Ala Ser Pro Arg Phe Gln Ser
        290                 295                 300

His Ala Thr Pro Arg Cys Leu Ser Pro Ala Leu Gln
305                 310                 315

<210> SEQ ID NO 11
<211> LENGTH: 478
<212> TYPE: DNA
<213> ORGANISM: Homo sapiens
<220> FEATURE:
<221> NAME/KEY: CDS
<222> LOCATION: (19)..(249)
```

-continued

<400> SEQUENCE: 11

```
cccacgcgtc cgggcaac atg ggg tcc agc agc ttc ttg gtc ctc atg gtg        51
                    Met Gly Ser Ser Ser Phe Leu Val Leu Met Val
                     1               5                  10 tct ctc gtt ctt gtg acc ctg gtg gct gtg gaa gga gtt aaa gag ggt        99
Ser Leu Val Leu Val Thr Leu Val Ala Val Glu Gly Val Lys Glu Gly
            15                  20                  25 ata gag aaa gca ggg gtt tgc cca gct gac aac gta cgc tgc ttc aag       147
Ile Glu Lys Ala Gly Val Cys Pro Ala Asp Asn Val Arg Cys Phe Lys
    30                  35                  40 tcc gat cct ccc cag tgt cac aca gac cag gac tgt ctg ggg gaa agg       195
Ser Asp Pro Pro Gln Cys His Thr Asp Gln Asp Cys Leu Gly Glu Arg
45                  50                  55 aag tgt tgt tac ctg cac tgt ggc ttc aag tgt gtg att cct gtg aag       243
Lys Cys Cys Tyr Leu His Cys Gly Phe Lys Cys Val Ile Pro Val Lys
 60                  65                  70                  75 aac tga agaaggagga acaaggatg aagatgtgtc aaggccatac cctgagccag         299
Asn gatgggaagg ccaagtgtcc aggctcctcc tctacaccag gtgtcctcag aaatgatgct     359 gggtccttc tacctctggg ggtcatctca cttggcacct gcccctgagg tcctgagact      419
tggaatatgg aagaagcaat acccaacccc accaaagaaa acctgagctg aagtcctttt    478
```

<210> SEQ ID NO 12
<211> LENGTH: 76
<212> TYPE: PRT
<213> ORGANISM: Homo sapiens

<400> SEQUENCE: 12

```
Met Gly Ser Ser Ser Phe Leu Val Leu Met Val Ser Leu Val Leu Val
 1               5                  10                  15

Thr Leu Val Ala Val Glu Gly Val Lys Glu Gly Ile Glu Lys Ala Gly
            20                  25                  30

Val Cys Pro Ala Asp Asn Val Arg Cys Phe Lys Ser Asp Pro Pro Gln
        35                  40                  45

Cys His Thr Asp Gln Asp Cys Leu Gly Glu Arg Lys Cys Cys Tyr Leu
    50                  55                  60

His Cys Gly Phe Lys Cys Val Ile Pro Val Lys Asn
65                  70                  75
```

<210> SEQ ID NO 13
<211> LENGTH: 733
<212> TYPE: DNA
<213> ORGANISM: Homo sapiens

<400> SEQUENCE: 13

```
gggatccgga gcccaaatct ctgacaaaa ctcacacatg cccaccgtgc ccagcacctg        60
aattcgaggg tgcaccgtca gtcttcctct ccccccaaa acccaaggac accctcatga      120
tctcccggac tcctgaggtc acatgcgtgg tggtggacgt aagccacgaa gaccctgagg     180
tcaagttcaa ctggtacgtg acggcgtgg aggtgcataa tgccaagaca aagccgcggg     240
aggagcagta caacagcacg taccgtgtgg tcagcgtcct caccgtcctg caccaggact     300
ggctgaatgg caaggagtac aagtgcaagg tctccaacaa agccctccca ccccccatcg    360
agaaaaccat ctccaaagcc aaagggcagc ccgagaacc acaggtgtac accctgcccc      420
catcccggga tgagctgacc aagaaccagg tcagcctgac ctgcctggtc aaaggcttct     480
atccaagcga catcgccgtg gagtgggaga gcaatgggca gccggagaac aactacaaga    540
```

```
ccacgcctcc cgtgctggac tccgacggct ccttcttcct ctacagcaag ctcaccgtgg      600
acaagagcag gtggcagcag gggaacgtct tctcatgctc cgtgatgcat gaggctctgc      660
acaaccacta cacgcagaag agcctctccc tgtctccggg taaatgagtg cgacggccgc      720
gactctagag gat                                                         733
```